US011213643B2

(12) United States Patent
Burgess et al.

(10) Patent No.: US 11,213,643 B2
(45) Date of Patent: Jan. 4, 2022

(54) FLOW PATH SENSING FOR FLOW THERAPY APPARATUS

(71) Applicant: Fisher & Paykel Healthcare Limited, Auckland (NZ)

(72) Inventors: Russel William Burgess, Auckland (NZ); Dean Antony Barker, Auckland (NZ); Kevin Peter O'Donnell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 268 days.

(21) Appl. No.: 16/301,952

(22) PCT Filed: May 17, 2017

(86) PCT No.: PCT/NZ2017/050063
§ 371 (c)(1),
(2) Date: Nov. 15, 2018

(87) PCT Pub. No.: WO2017/200394
PCT Pub. Date: Nov. 23, 2017

(65) Prior Publication Data
US 2019/0217030 A1 Jul. 18, 2019

Related U.S. Application Data

(60) Provisional application No. 62/507,013, filed on May 16, 2017, provisional application No. 62/337,795, filed on May 17, 2016.

(51) Int. Cl.
*A61M 16/00* (2006.01)
*A61M 16/10* (2006.01)
(Continued)

(52) U.S. Cl.
CPC ......... *A61M 16/0069* (2014.02); *A61B 5/087* (2013.01); *A61B 5/0816* (2013.01);
(Continued)

(58) Field of Classification Search
CPC .............. A61M 16/00; A61M 16/0069; A61M 16/026; A61M 16/109; A61M 16/16;
(Continued)

(56) References Cited

U.S. PATENT DOCUMENTS 6,532,959 B1 3/2003 Berthon-Jones
7,942,824 B1 5/2011 Kayyali et al.
(Continued)

FOREIGN PATENT DOCUMENTS

EP 2753390 B1 11/2016
WO WO 2002/028460 A1 4/2002
(Continued)

OTHER PUBLICATIONS

International Search Report in corresponding International Patent Application No. PCT/NZ2017/050063, dated Oct. 9, 2017, in 14 pages.
(Continued)

*Primary Examiner* — Joseph D. Boecker
(74) *Attorney, Agent, or Firm* — Knobbe, Martens, Olson & Bear, LLP

(57) ABSTRACT

Systems and method for conducting respiratory therapy in a respiratory system can adjust a flow of respiratory gases to a patient based upon a detected patient breath cycle. The respiratory system can include a non-sealed patient interface. The respiratory system can be configured to deliver a high flow therapy. A patient breath cycle may be determined using one or more measured parameters, such as a flow rate, a blower motor speed, and/or a system pressure. A flow source may be adjusted to have a phase matching that of the
(Continued)

patient's breath cycle, such that flow in increased in response to the patient inhaling, and decreased in response to the patient exhaling.

21 Claims, 17 Drawing Sheets

(51) Int. Cl.
| | | |
|---|---|---|
| *A61B 5/08* | (2006.01) | |
| *A61B 5/00* | (2006.01) | |
| *A61B 5/087* | (2006.01) | |
| *A61M 16/16* | (2006.01) | |

(52) U.S. Cl.
CPC ......... *A61B 5/4836* (2013.01); *A61M 16/026* (2017.08); *A61M 16/109* (2014.02); *A61M 16/16* (2013.01); *A61B 5/0878* (2013.01); *A61B 5/7246* (2013.01); *A61M 16/161* (2014.02); *A61M 2016/0027* (2013.01); *A61M 2016/0039* (2013.01); *A61M 2205/3365* (2013.01); *A61M 2205/3368* (2013.01); *A61M 2205/3375* (2013.01); *A61M 2205/3569* (2013.01); *A61M 2205/3592* (2013.01); *A61M 2230/205* (2013.01)

(58) Field of Classification Search
CPC ........ A61M 16/161; A61M 2016/0018; A61M 2016/0027; A61M 2016/0036; A61M 2016/0039; A61M 2016/0066; A61M 2016/022; A61M 2016/024; A61M 2205/3331; A61M 2205/3334; A61M 2205/3344; A61B 5/0816; A61B 5/087; A61B 5/0878; A61B 5/7246
See application file for complete search history.

(56) References Cited

U.S. PATENT DOCUMENTS

| | | |
|---|---|---|
| 2005/0005937 A1* | 1/2005 | Farrugia ............ A61M 16/024 128/204.18 |
| 2013/0228181 A1 | 9/2013 | Ahmad et al. |
| 2014/0326241 A1 | 11/2014 | Martin et al. |
| 2015/0059745 A1* | 3/2015 | Barker ............ A61M 16/0069 128/203.14 |
| 2015/0136136 A1* | 5/2015 | Fleming ................ A61B 5/087 128/204.23 |
| 2016/0015918 A1 | 1/2016 | Kuriger et al. |
| 2016/0121063 A1* | 5/2016 | Tatkov ................ A61M 16/024 128/204.23 |
| 2016/0243325 A1* | 8/2016 | Bowman ........... A61M 16/0069 |
| 2018/0221608 A1* | 8/2018 | Schwaibold ........ A61M 16/024 |

FOREIGN PATENT DOCUMENTS

| | | |
|---|---|---|
| WO | WO 2002/094358 A1 | 11/2002 |
| WO | WO 2004/112680 A2 | 12/2004 |
| WO | WO 2005/063323 A1 | 7/2005 |
| WO | WO 2009/149351 A1 | 12/2009 |
| WO | WO 2013/057635 A1 | 4/2013 |
| WO | WO 2013/163685 A1 | 11/2013 |
| WO | WO 2013/163687 A1 | 11/2013 |
| WO | WO 2013/173219 A1 | 11/2013 |
| WO | WO 2014/196875 A1 | 12/2014 |
| WO | WO 2015/000025 A1 | 1/2015 |
| WO | WO 2017/077417 A1 | 5/2017 |
| WO | WO 2017/200394 A1 | 11/2017 |

OTHER PUBLICATIONS

Written Opinion in corresponding International Patent Application No. PCT/NZ2017/050063, dated Oct. 9, 2017, in 12 pages.
International Preliminary Report on Patentability in corresponding International Patent Application No. PCT/NZ2017/050063, dated Nov. 20, 2018, in 13 pages.

* cited by examiner

FLOW PATH SENSING FOR FLOW THERAPY APPARATUS

FIELD OF THE DISCLOSURE

Any and all applications for which a foreign or domestic priority claim is identified in the Application Data Sheet as filed with the present application are hereby incorporated by reference under 37 CFR 1.57.

BACKGROUND

Breathing assistance apparatuses are used in various environments such as hospital, medical facility, residential care, or home environments to deliver a flow of gas to users or patients. A breathing assistance apparatus, or a flow therapy apparatus, may include a valve used to deliver oxygen with the flow of gas, and/or a humidification apparatus to deliver heated and humidified gases. A flow therapy apparatus may allow adjustment and control over characteristics of the gas flow, including flow rate, temperature, gas concentration, humidity, pressure, etc. Sensors, such as heated temperature sensing elements and/or thermistors, are used to measure these properties of the gases.

SUMMARY

The present disclosure describes a flow therapy apparatus which may be used to provide a flow of gases to a patient in a non-sealed or sealed system. The flow of respiratory gases can be adjusted based upon a detected breath cycle of the patient. The patient breath cycle may be determined using one or more measured parameters, such as a flow rate, a blower motor speed, and/or a system pressure. A flow source may be controlled using a periodic waveform, which is adjusted to have a phase based upon that of the patient's breath cycle, such that flow is adjusted in response to the patient inhaling and exhaling.

A method for conducting respiratory therapy in a respiratory system is provided. The method can comprise driving a blower motor using a control signal, the blower motor configured to generate an air flow to a patient. The method can further comprise detecting a breath cycle of the patient by receiving a first sensor input comprising one or more flow measurements from at least one flow sensor, receiving a second sensor input comprising one or more pressure measurements from at least one pressure sensor or one or more motor speed measurements associated with the blower motor, and generating a breath cycle waveform using at least the received flow measurements, wherein the breath cycle waveform can comprise a plurality of alternating inspiration and expiration periods by the patient. The method can further comprise synchronizing the control signal with the breath cycle by identifying a phase of the breath cycle waveform, and iteratively updating a phase of the control signal to achieve a determined phase difference between the control signal and the breath cycle waveform, such that the control signal can be configured to adjust a speed of the blower motor based upon the patient's inspiration and expiration. The method can further comprise phase-shifting the control signal based upon a system delay between the control signal being received by the blower motor and the one or more flow measurements. The method can further comprise phase-shifting the control signal, such that the control signal can pre-empt the breath cycle waveform by a set amount of time. The at least one flow sensor can comprise an ultrasonic sensor assembly. The at least one flow sensor can further comprise a heated temperature sensing element. The control signal can be phase-locked to the breath cycle waveform. A magnitude of the control signal can be determined based at least in part upon an amplitude of the breath cycle waveform, a positive feedback parameter, and a negative feedback parameter. The second input sensor can be the one or more motor speed measurements associated with the blower motor. The breath cycle waveform can be generated using the received flow and motor speed measurements. The breath cycle waveform can be generated based at least in part upon a flow restriction calculated using the received flow and motor speed measurements. The breath cycle waveform can be generated based at least in part upon a calculated patient flow, wherein the patient flow can be based upon a system leak calculated using the received flow and motor speed measurements. The motor speed measurements can be determined based at least in part upon one or more blower motor parameters. The blower motor can comprise a brushless DC motor. Detecting a breath cycle of the patient can comprise receiving a third sensor input, the third sensor input comprising the one or more pressure measurements from the at least one pressure sensor. The second input sensor can be the one or more pressure measurements from the at least one pressure sensor. The method for conducting respiratory therapy can be conducted in a high flow respiratory system. The method for conducting respiratory therapy can be conducted in a non-sealed respiratory system. The method for conducting respiratory therapy can be conducted in a sealed respiratory system. The method can further comprise adjusting a motor speed to achieve a predetermined pressure of the system based on the one or more pressure measurements from the at least one pressure sensor. The sealed respiratory system can comprise a non-invasive ventilation mask. The pressure sensor can be located in the non-invasive ventilation mask, or a manifold connecting the non-invasive ventilation mask to a patient breathing conduit, or within the patient breathing conduit, or within a housing of the respiratory system. The system may have a memory for storing data. The stored data can comprise respiratory rate, treatment time, motor speed, flow rate, and/or pressure. The memory may be an EEPROM.

A respiratory therapy apparatus is provided. The apparatus can comprise a blower for generating an air flow for a patient, the blower being associated with a motor, wherein the motor can be configured to be driven by a control signal. The apparatus can further comprise one or more sensors configured to measure at least a flow rate, the one or more sensor further configured to measure a motor speed or pressure. The apparatus can further comprise a control system configured to detect a breath cycle of the patient by receiving a first sensor input comprising one or more flow measurements from at least one flow sensor, receiving a second sensor input comprising one or more pressure measurements from at least one pressure sensor or one or more motor speed measurements associated with the blower motor, and generating a breath cycle waveform using at least the received flow measurements, wherein the breath cycle waveform can comprise a plurality of alternating inspiration and expiration periods by the patient. The control system can be further configured to synchronize the control signal with the breath cycle by identifying a phase of the breath cycle waveform, and iteratively updating a phase of the control signal to achieve a determined phase difference between the control signal and the breath cycle waveform, such that the control signal can be configured to adjust a speed of the blower motor based upon the patient's inspiration and expiration. The control signal can be further configured to phase-shift the control signal based upon a system delay between the control signal being received by the blower motor and the resulting air flow being sensed. The control signal can be further configured to phase-shift the control signal, such that the control signal can pre-empt the breath cycle waveform by a set amount of time. The at least one flow sensor can comprise an ultrasonic sensor assembly. The at least one flow sensor can further comprise a heated temperature sensing element. The control signal can be phase-locked to the breath cycle waveform. The breath cycle waveform can be used to calculate a patient breath rate. A magnitude of the control signal can be determined based at least in part upon an amplitude of the breath cycle waveform, a positive feedback parameter, and a negative feedback parameter. The second input sensor can be the one or more motor speed measurements associated with the blower motor. The breath cycle waveform can be generated using the received flow and motor speed measurements. The breath cycle waveform can be generated based at least in part upon a calculated patient flow, wherein the patient flow can be based upon a system leak calculated using the received flow and motor speed measurements. The motor speed measurements can be determined based at least in part upon one or more blower motor parameters. The blower motor can comprise a brushless DC motor. The control system can be configured to detect the breath cycle by receiving a third sensor input, the third sensor input comprising the one or more pressure measurements from the at least one pressure sensor. The second input sensor can be the one or more pressure measurements from the at least one pressure sensor. The respiratory therapy apparatus can be a respiratory high flow therapy apparatus. The respiratory therapy apparatus can be configured for use in a non-sealed respiratory system. The respiratory therapy apparatus can be configured for use in a sealed respiratory system. The respiratory therapy apparatus can be configured to adjust a motor speed to achieve a predetermined pressure of the sealed respiratory system based on the one or more pressure measurements from the pressure sensor. The respiratory therapy apparatus can be configured to be coupled with a non-invasive ventilation mask. The pressure sensor can be located in the non-invasive ventilation mask, or a manifold connecting the non-invasive ventilation mask to a patient breathing conduit, or within the patient breathing conduit, or within a housing of the respiratory therapy apparatus. The apparatus may have a memory for storing data. The stored data can comprise respiratory rate, treatment time, motor speed, flow rate, and/or pressure. The memory may be an EEPROM.

A method for adjusting a flow rate of a respiratory system according to patient inspiration and expiration. The method comprising receiving at a processor a first input corresponding to the flow rate of an air flow generated by a source based at least in part upon a control signal; receiving at the processor at least a second input; and determining by the processor a predicted respiration cycle of the patient, based at least in part upon the first and second inputs. The method can further comprise adjusting the control signal based at least in part upon an amplitude of the predicted respiration cycle using a positive feedback parameter. The method can further comprise adjusting the control signal based at least in part upon an amplitude of the predicted respiration cycle using a negative feedback parameter. The method can further comprise adjusting the control signal for the source, wherein adjusting the control signal comprises performing at least one phase-locked loop iteration on the control signal against the predicted respiration cycle, such that a phase of the control signal substantially can match a phase of the predicted respiration cycle by a determined phase difference. The second input can correspond to a speed of a motor associated with the source. The method further comprises receiving a third input, the third input comprising pressure. The second input can correspond to pressure. Adjusting the control signal can further comprise phase-shifting the control signal relative to the predicted respiration cycle. Adjusting the control signal can further comprise phase-shifting the control signal relative to the predicted respiration cycle, based at least in part upon a system delay. Adjusting the control signal can further comprise phase-shifting the control signal relative to the predicted respiration cycle to pre-empt the predicted respiration cycle by a designated amount. The method can be used in a non-sealed or sealed respiratory system. The system may have a memory for storing data. The stored data can comprise respiratory rate, treatment time, motor speed, flow rate, and/or pressure. The memory may be an EEPROM.

A system configured to adjust a flow rate according to patient inspiration and expiration is provided. The system can comprise a source configured to generate the air flow, based at least in part upon a control signal. The system can further comprise a processor configured to receive a first input corresponding to a flow rate of the air flow, receive at least a second input, and determine a predicted respiration cycle of the patient, based at least in part upon the first and second inputs. The processor can be configured to adjust the control signal based at least in part upon an amplitude of the predicted respiration cycle using a positive feedback parameter. The processor can be configured to adjust the control signal based at least in part upon an amplitude of the predicted respiration cycle using a negative feedback parameter. The processor can be further configured to adjust the control signal for the source, wherein adjusting the control signal can comprise performing at least one phase-locked loop iteration on the control signal against the predicted respiration cycle, such that a phase of the control signal can substantially match a phase of the predicted respiration cycle by a determined phase difference. Adjusting the control signal can further comprise phase-shifting the control signal relative to the predicted respiration cycle. The control signal can be phase-shifted relative to the predicted respiration cycle, based at least in part upon a system delay. The control signal can be phase-shifted relative to the predicted respiration cycle to pre-empt the predicted respiration cycle by a designated amount. The processor can be further configured to calculate a patient breath rate, based at least in part upon the predicted respiration cycle of the patient. The second input can correspond to a speed of a motor associated with the source. The processor can be configured to receive a third input, the third input comprising pressure. The second input sensor can correspond to pressure. The system can comprise a high flow system. The system can be a non-sealed respiratory system. The system can be a sealed respiratory system. The respiratory therapy apparatus configured to adjust a motor speed to achieve a predetermined pressure of the system based on one or more pressure measurements from at least one pressure sensor. The system can comprise a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory system. The system may have a memory for storing data. The stored data can comprise respiratory rate, treatment time, motor speed, flow rate, and/or pressure. The memory may be an EEPROM.

A method for adjusting a control waveform for a respiratory assistance apparatus is provided. The method can comprise detecting a breath cycle of a patient, synchronizing the control waveform with the detected breath cycle, and phase-shifting the control waveform relative to the detected breath cycle. The control waveform can be phase-shifted to have a determined phase difference relative to the breath cycle. Synchronizing the control waveform with the detected breath cycle can comprise enhancing the breath cycle using positive feedback. Synchronizing the control waveform with the detected breath cycle can comprise regulating the breath cycle using negative feedback, wherein negative feedback can be applied to the breath cycle when a magnitude of the breath cycle satisfies a threshold amount. The control waveform can be a phase-locked loop relative to the detected breath cycle. The phase-locked loop can progressively reduce error between the control waveform and the detected breath cycle each cycle. The control waveform can be phase-shifted by an amount to compensate for a system delay associated with the respiratory assistance apparatus. The control waveform can be phase-shifted by an amount to pre-empt the breath cycle. The respiratory assistance apparatus can comprise at least one flow sensor. The at least one flow sensor can comprise an ultrasonic sensor assembly. Flow feedback can be received from the at least one flow sensor. The respiratory assistance apparatus can comprise a blower. The blower can comprise a motor. Motor speed feedback can be received from the blower motor. The motor can be a brushless DC motor, which can be configured to provide sensorless feedback. The motor can be a low inertia motor. The method can further comprise driving a blower motor using the phase-shifted control waveform. The respiratory assistance apparatus can comprise a blower comprising a motor and at least one flow sensor, and the method can further comprise receiving feedback variables from the motor and the least one flow sensor, wherein the received motor and flow sensor feedback variables can be computed, in combination, to produce a breath cycle waveform. Motor speed feedback can be received from the blower motor. The feedback from the motor can include indication of system pressure. The respiratory system can comprise a pressure sensor. The received pressure and flow sensor feedback variables can be computed, in combination, to produce a breath cycle waveform. The received pressure, motor, and flow sensor feedback variables can be computed, in combination, to produce a breath cycle waveform. The method for conducting respiratory therapy may be conducted a high flow respiratory system. The method for conducting respiratory therapy may be conducted in a non-sealed respiratory system. The method for conducting respiratory therapy may be conducted in a sealed respiratory system. The method can further comprise adjusting a motor speed to achieve a predetermined pressure of the system based on pressure measurements by the pressure sensor. The sealed respiratory system can comprise a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory system. The system may have a memory for storing data. The stored data can comprise respiratory rate, treatment time, motor speed, flow rate, and/or pressure. The memory may be an EEPROM.

A respiratory assistance apparatus configured to adjust a flow rate according to patient inspiration and expiration is provided. The apparatus can comprise a blower comprising a motor. The apparatus can further comprise at least one sensor to measure a flow rate. The apparatus can further comprise a processor configured to determine a predicted cycle of inspiration and expiration of a patient based at least on the flow rate, and adjust a flow of the respiratory gases in accordance with patient respiration. The at least one sensor can comprise first and second ultrasonic transducers. The at least one sensor can comprise a heated temperature sensing element. The at least one sensor can comprise both first and second ultrasonic transducers and a heated temperature sensing element. The flow of the respiratory gases can be adjusted based at least in part upon a bi-stable system using both positive and negative feedback. The processor can determine the predicted cycle of inspiration and expiration of the patient based on the flow rate and the signal indicative of a blower motor speed, the motor configured to provide a signal indicative of the blower motor speed. The respiratory assistance apparatus can further comprise a pressure sensor to measure pressure. The processor can determine the predicted cycle of inspiration and expiration of the patient based on the flow rate and pressure. The processor can determine the predicted cycle of inspiration and expiration of the patient based on the flow rate, the motor speed, and the pressure. The respiratory assistance apparatus can be a high flow respiratory assistance apparatus. The respiratory therapy apparatus can be configured for use in a non-sealed respiratory system. The respiratory therapy apparatus can be configured for use in a sealed respiratory system. The respiratory therapy apparatus can be configured to adjust a motor speed to achieve a predetermined pressure of the sealed respiratory system based on the pressure measured by the pressure sensor. The respiratory therapy apparatus can be configured to be coupled with a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory assistance apparatus. The apparatus may have a memory for storing data. The stored data can comprise respiratory rate, treatment time, motor speed, flow rate, and/or pressure. The memory may be an EEPROM.

A system configured to adjust a flow rate according to patient inspiration and expiration is provided. The system can comprise a blower and a processor. The processor can be configured to receive a first input corresponding to flow rate, and a second input. The processor can be further configured to determine a predicted cycle of inspiration and expiration of a patient based on the first and second inputs, and adjust a flow of the respiratory gases in accordance with the predicted cycle of inspiration and expiration of the patient. The flow rate can be determined using first and second ultrasonic transducers. The flow rate can be determined using a heated temperature sensing element. The flow rate can be determined using first and second of ultrasonic transducers in combination with a heated temperature sensing element. The flow of the respiratory gases can be adjusted based at least in part upon a bi-stable system using both positive and negative feedback. The second input can be motor speed feedback means configured to provide a signal indicative of a blower motor speed. The processor can be configured to receive a third input, the third input comprising pressure. The second input can be pressure from a pressure sensor. The system can be a high flow system. The respiratory therapy apparatus can be configured for use in a non-sealed respiratory system. The respiratory therapy apparatus can be configured for use in a sealed respiratory system. The respiratory therapy apparatus can be configured to adjust a motor speed to achieve a predetermined pressure of the sealed respiratory system based on pressure from the pressure sensor. The respiratory therapy apparatus can be configured to be coupled with a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory therapy apparatus. The second input can be pressure in addition to motor feedback. The system may have a memory for storing data. The stored data can comprise respiratory rate, treatment time, motor speed, flow rate, and/or pressure. The memory may be an EEPROM.

A respiratory system configured to determine a patient's respiratory rate is provided. The system can comprise at least one sensor configured to measure a flow rate; a processor configured to be in electrical communication with the at least one sensor to receive flow rate measurements of the patient using the respiratory system, the processor further configured to determine the patient's respiratory rate by autocorrelating a plot of the flow rate measurements with respect to time. The processor can be configured to determine a breath cycle from one or more peaks or zero-crossings of the autocorrelation of the plot of the flow rate measurements with respect to time. The at least one sensor can comprise first and second ultrasonic transducers. The at least one sensor can comprise a heated temperature sensing element. The at least one sensor can comprise both first and second ultrasonic transducers and a heated temperature sensing element. The processor can be configured to generate a breath cycle waveform based at least in part on the determined respiratory rate, wherein the breath cycle waveform can comprise a plurality of alternating inspiration and expiration periods by the patient. The system can further comprise a blower for generating an air flow for a patient, the blower being associated with a motor, wherein the motor can be configured to be driven by a control signal. The blower motor can comprise a brushless DC motor. The processor can be configured to synchronize the control signal with the breath cycle by identifying a phase of the breath cycle waveform, and iteratively updating a phase of the control signal to achieve a determined phase difference between the control signal and the breath cycle waveform, such that the control signal can be configured to adjust a speed of the blower motor based upon the patient's inspiration and expiration. The processor can be further configured to phase-shift the control signal based upon a system delay between the control signal being received by the blower motor and the resulting air flow being sensed. The processor can be further configured to phase-shift the control signal, such that the control signal can pre-empt the breath cycle waveform by a set amount of time. The processor can be configured to generate a breath cycle waveform based on the flow rate measurements and motor speed measurements associated with the blower motor. The motor speed measurements can be determined based at least in part upon one or more blower motor parameters. Generating a breath cycle waveform can be based on the flow rate measurements and one or more pressure measurements from a pressure sensor. Generating a breath cycle waveform can based on the flow rate measurements, the motor speed measurements, and the one or more pressure measurements from the pressure sensor. The respiratory system can comprise a respiratory high flow therapy apparatus. The respiratory system can be a non-sealed respiratory system. The respiratory system can be a sealed respiratory system. The processor can be configured to adjust a motor speed to achieve a predetermined pressure of the system based on the one or more pressure measurements from the pressure sensor. The respiratory system can comprise a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory system. The system may have a memory for storing data. The stored data can comprise respiratory rate, treatment time, motor speed, flow rate, and/or pressure. The memory may be an EEPROM.

A method for determine a patient's respiratory rate using a respiratory system is provided. The method can comprise receiving flow rate measurements of a patient using the respiratory system from at least one sensor; autocorrelating a plot of the flow rate measurements with respect to time; and determining the patient's respiratory rate from the autocorrelation. Determining the patient's respiratory rate can further comprise determining the patient's breath cycle from one or more peaks or zero-crossings in the autocorrelation. The flow rate measurements can be made by first and second ultrasonic transducers. The flow rate measurements can be made by a heated temperature sensing element. The flow rate measurements can be made by both first and second ultrasonic transducers and a heated temperature sensing element. The method can further comprise generating a breath cycle waveform based at least in part on the determined respiratory rate, wherein the breath cycle waveform can comprise a plurality of alternating inspiration and expiration periods by the patient. The respiratory system can comprise a blower for generating an air flow for a patient, the blower being associated with a motor, wherein the motor can be configured to be driven by a control signal. The blower motor comprises a brushless DC motor. The method can further comprise synchronizing the control signal with the breath cycle by identifying a phase of the breath cycle waveform, and iteratively updating a phase of the control signal to achieve a determined phase difference between the control signal and the breath cycle waveform, such that the control signal can be configured to adjust a speed of the blower motor based upon the patient's inspiration and expiration. Synchronizing can further comprise phase-shifting the control signal based upon a system delay between the control signal being received by the blower motor and the resulting air flow being sensed by a patient. Synchronizing can further comprise phase-shifting the control signal, such that the control signal can pre-empt the breath cycle waveform by a set amount of time. The method can further comprise generating a breath cycle waveform based on the determined respiratory rate and motor speed measurements associated with the blower motor. The method can further comprise determining the motor speed measurements based upon the one or more blower motor parameters. Generating a breath cycle waveform can be based on the determined respiratory rate and one or more pressure measurements from a pressure sensor. Generating a breath cycle waveform can be based on the determined respiratory rate, the one or more blower motor parameters, and the one or more pressure measurements from the pressure sensor. The respiratory system can comprise a respiratory high flow therapy apparatus. The respiratory system can be a non-sealed respiratory system. The respiratory system can be a sealed respiratory system. The processor can be configured to adjust a motor speed to achieve a predetermined pressure of the system based on the pressure measurements from the pressure sensor. The respiratory system can comprise a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory system. The system may have a memory for storing data. The stored data can comprise respiratory rate, treatment time, motor speed, flow rate, and/or pressure. The memory may be an EEPROM.

A respiratory therapy apparatus is provided. The respiratory therapy apparatus can comprise a blower for generating an air flow for a patient, the blower being associated with a motor, wherein the motor can be configured to be driven by a control signal; one or more sensors configured to measure at least a flow rate; and a control system configured to detect a breath cycle of the patient by receiving one or more flow measurements from the one or more sensors, and generating a breath cycle waveform using at least the received flow, wherein the breath cycle waveform can comprise a plurality of alternating inspiration and expiration periods by the patient, and identifying a phase difference between the control signal and the breath cycle waveform from a cross-correlation of the control signal and the breath cycle waveform. The control system can be configured to determine the phase difference from one or more peaks or zero-crossings of the cross-correlation of the control signal and the breath cycle waveform. The control system can be configured to synchronize the control signal with the breath cycle by iteratively updating a phase of the control signal to achieve a predetermined phase difference between the control signal and the breath cycle waveform based on the identified phase difference, such that the control signal can be configured to adjust a speed of the blower motor based upon the patient's inspiration and expiration. The control system can be further configured to phase-shift the control signal based upon a system delay between the control signal being received by the blower motor and the resulting air flow being sensed by the patient. The control system can be further configured to phase-shift the control signal, such that the control signal can pre-empt the breath cycle waveform by a set amount of time. The one or more sensors can comprise an ultrasonic sensor assembly. The one or more sensors can further comprise a heated temperature sensing element. The control signal can be phase-locked to the breath cycle waveform. The breath cycle waveform can be used to calculate a patient breath rate. A patient breath rate can be calculated from an auto-correlation of the flow rate measurements over time. The patient breath cycle can be determined from one or more peaks or zero-crossings in the autocorrelation. A magnitude of the control signal can be determined based at least in part upon an amplitude of the breath cycle waveform, a positive feedback parameter, and a negative feedback parameter. The breath cycle waveform can be generated based on the received flow and motor speed measurements associated with the blower motor. The breath cycle waveform can be generated based at least in part upon a calculated patient flow, wherein the patient flow is based upon a system leak calculated using the received flow and the motor speed measurements associated with the blower motor. The motor speed measurements can be determined based at least in part upon one or more blower motor parameters. The blower motor can comprise a brushless DC motor. The control system can be configured to generate a breath cycle waveform based on the received flow and one or more pressure measurements from a pressure sensor. The control system can be configured to generate a breath cycle waveform based on the received flow, the motor speed measurements associated with the blower motor, and the one or more pressure measurements from a pressure sensor. The respiratory therapy apparatus can be a respiratory high flow therapy apparatus. The respiratory therapy apparatus can be configured for use in a non-sealed respiratory system. The respiratory therapy apparatus can be configured for use in a sealed respiratory system. The respiratory therapy apparatus can be configured to adjust a motor speed to achieve a predetermined pressure of the sealed respiratory system based on the pressure measurements from the pressure sensor. The respiratory therapy apparatus can be configured to be coupled with a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory therapy apparatus. The system may have a memory for storing data. The stored data can comprise respiratory rate, treatment time, motor speed, flow rate, and/or pressure. The memory may be an EEPROM.

A method for conducting respiratory therapy in a respiratory system is disclosed. The method can comprise driving a blower motor using a control signal, the blower motor configured to generate an air flow to a patient; detecting a breath cycle of the patient by receiving one or more flow measurements from at least one flow sensor; and generating a breath cycle waveform using at least the received flow, wherein the breath cycle waveform can comprise a plurality of alternating inspiration and expiration periods by the patient; and identifying a phase difference between the control signal and the breath cycle waveform from a cross-correlation of the control signal and the breath cycle waveform. Identifying can further comprise determining the phase difference from one or more peaks or zero-crossings of the cross-correlation of the control signal and the breath cycle waveform. The method can further comprise synchronizing the control signal with the breath cycle by iteratively updating a phase of the control signal to achieve a predetermined phase difference between the control signal and the breath cycle waveform based on the identified phase difference, such that the control signal can be configured to adjust a speed of the blower motor based upon the patient's inspiration and expiration. Synchronizing can further comprise phase-shifting the control signal based upon a system delay between the control signal being received by the blower motor and the resulting air flow being sensed by the patient. Synchronizing can further comprise phase-shifting the control signal, such that the control signal can pre-empt the breath cycle waveform by a set amount of time. The at least one flow sensor can comprise an ultrasonic sensor assembly. The at least one flow sensor can comprise a heated temperature sensing element. The method can further comprise phase-locking the control signal to the breath cycle waveform. The breath cycle waveform can be used to calculate a patient breath rate. Detecting can further comprise calculating a patient breath rate from an auto-correlation of the flow rate measurements over time. The patient breath cycle can be determined from one or more peaks or zero-crossings in the autocorrelation. A magnitude of the control signal can be determined based at least in part upon an amplitude of the breath cycle waveform, a positive feedback parameter, and a negative feedback parameter. The breath cycle waveform can be generated based on the one or more flow measurements and motor speed measurements associated with the blower motor. The breath cycle waveform can be generated based at least in part upon a flow restriction calculated using the received flow and motor speed measurements associated with the blower motor. The breath cycle waveform can be generated based at least in part upon a calculated patient flow, wherein the patient flow can be based upon a system leak calculated using the received flow and motor speed measurements. The motor speed measurements can be determined based at least in part upon one or more blower motor parameters. The blower motor can comprise a brushless DC motor. The breath cycle waveform can be generated based on the received flow and one or more pressure measurements from a pressure sensor. The breath cycle waveform can be generated based on the one or more flow measurements, the motor speed measurements associated with the blower motor, and the one or more pressure measurements from the pressure sensor. The method can be conducted in a high flow respiratory system. The method can be conducted in a non-sealed respiratory system. The method for conducting respiratory therapy can be conducted in a sealed respiratory system. The method can further comprise adjusting a motor speed to achieve a predetermined pressure of the system based on the pressure measurements from the pressure sensor. The sealed respiratory system can comprise a non-invasive ventilation mask. The pressure sensor can be located in the non-invasive ventilation mask or a manifold connecting the non-invasive ventilation mask to a patient breathing conduit, or within the patient breathing conduit, or within a housing of the respiratory system. The system may have a memory for storing data. The stored data can comprise respiratory rate, treatment time, motor speed, flow rate, and/or pressure. The memory may be an EEPROM.

DETAILED DESCRIPTION

Figure 1:
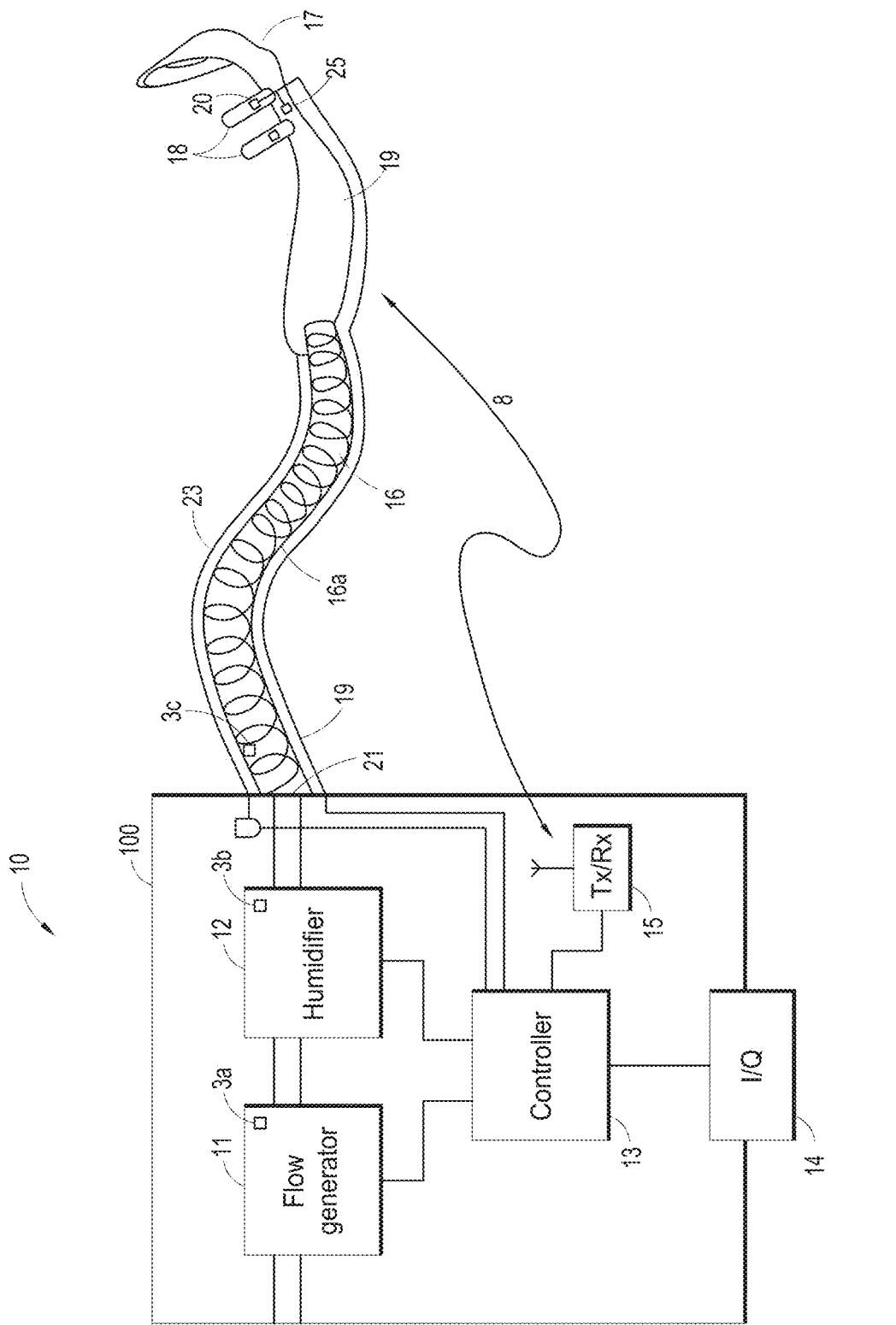
FIG. 1 shows in diagrammatic form an example breathing assistance apparatus in the form of a flow therapy apparatus.

A flow therapy apparatus 10 is shown in FIG. 1. In general terms, the apparatus 10 can comprise a main housing 100 that contains a flow generator 11 in the form of a motor/impeller arrangement, an optional humidifier 12, a controller 13, and a user interface 14 (comprising, for example, a display and input device(s) such as button(s), a touch screen, or the like). The controller 13 is configured or programmed to control the components of the apparatus, including: operating the flow generator 11 to create a flow of gas (gas flow) for delivery to a patient, operating the humidifier 12 (if present) to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gas flow output 21 in the housing 100 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. The gas flow, which may be humidified, is generated by the flow therapy apparatus 10 and delivered to the patient via the patient conduit 16 through the cannula 17. The patient conduit 16 can have a heater wire 16a to heat gas flow passing through to the patient. The heater wire 16a is under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will now be described. The controller 13 can control the flow generator 11 to generate a gas flow of the desired flow rate, control one or more valves to control a gas mix (for example, $O_2$ control), and/or control the humidifier 12 if present to humidify the gas flow and/or heat the gas flow to an appropriate level. The gas flow is directed out through the patient conduit 16 and cannula 17 to the patient. The controller 13 can also control a heating element in the humidifier 12 and/or the heating element 16a in the patient conduit 16 to heat the gas to a desired temperature that achieves a desired level of therapy and/or level of comfort for the patient. The controller 13 can be programmed with or can determine a suitable target temperature of the gas flow.

Operation sensors 3a, 3b, 3c, such as flow, temperature, humidity, and/or pressure sensors can be placed in various locations in the flow therapy apparatus 10. Additional sensors (e.g., sensors 20, 25) may be placed in various locations on the patient conduit 16 and/or cannula 17 (for example, there may be a temperature sensor at or near the end of the inspiratory tube). Output from the sensors can be received by the controller 13, to assist it to operate the flow therapy apparatus 10 in a manner that provides suitable therapy. Providing suitable therapy can include meeting a patient's inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. The apparatus 10 may have a memory for storing data, such as respiratory rate, treatment time, motor speed, flow rate, pressure, and the like. The memory may be, for example, an EEPROM. Additionally, or alternatively, the transmitter and/or receiver 15 may deliver data to a remote server or enable remote control of the apparatus 10.

The flow therapy apparatus 10 may comprise a high flow therapy apparatus. As used herein, "high flow" therapy may involve the administration of gas to the airways of a patient at a relatively high flow rate, for example, for adults, at least 15 L/min, or 20 L/min, or 25 L/min, or 30 L/min, or 40 L/min, or 50 L/min, or up to 150 L/min. For children and infants, the flow rate may be 1 L/min and up to 25 L/min, or 2 L/min, or 3 L/min, or 5 L/min, or 10 L/min, or 15 L/min, or 20 L/min. High flow therapy may be administered to the nares of a user and/or orally, or via a tracheostomy interface. High flow therapy may deliver gases to a user at a flow rate at or exceeding the intended user's peak inspiratory flow requirements. The high flow of gases reaching the patient's airways can be beneficial for flushing out the patient's airways, which can reduce the volume of anatomical dead space. High flow therapy is often delivered with a non-sealing patient interface such as, for example, a nasal cannula. The nasal cannula may be configured to deliver breathing gases to the nares of a user at a flow rate exceeding the intended user's peak inspiratory flow requirements.

The term "non-sealing patient interface" as used herein may refer to an interface providing a pneumatic link between an airway of a patient and a positive gas flow source (such as from flow generator 11) and that that does not completely occlude the airway of the patient. Non-sealed pneumatic link can comprise an occlusion of less than 95% of the airway of the patient. The non-sealed pneumatic link can comprise an occlusion of less than 90% of the airway of the patient. The non-sealed pneumatic link can comprise an occlusion of between 40% and 80% of the airway of the patient. The airway can be one or more of a nare or mouth of the patient.

The system described herein may also be used with a sealed patient interface. Non-limiting examples of a sealed patient interface can include non-invasive ventilation (NIV) full face and nasal masks. NIV masks can support a patient's breathing without the need for intubation or a tracheostomy. NIV masks can have a patient interface that contours to the patient's face to provide a sealed fit between the mask and the patient's face.

Additional details of an example flow therapy apparatus is disclosed in U.S. Provisional Application Ser. No. 62/262, 325, titled "Flow Path Sensing for Flow Therapy Apparatus", filed on Dec. 2, 2015, which is hereby incorporated by reference in its entirety.

Control System

Figure 2A:
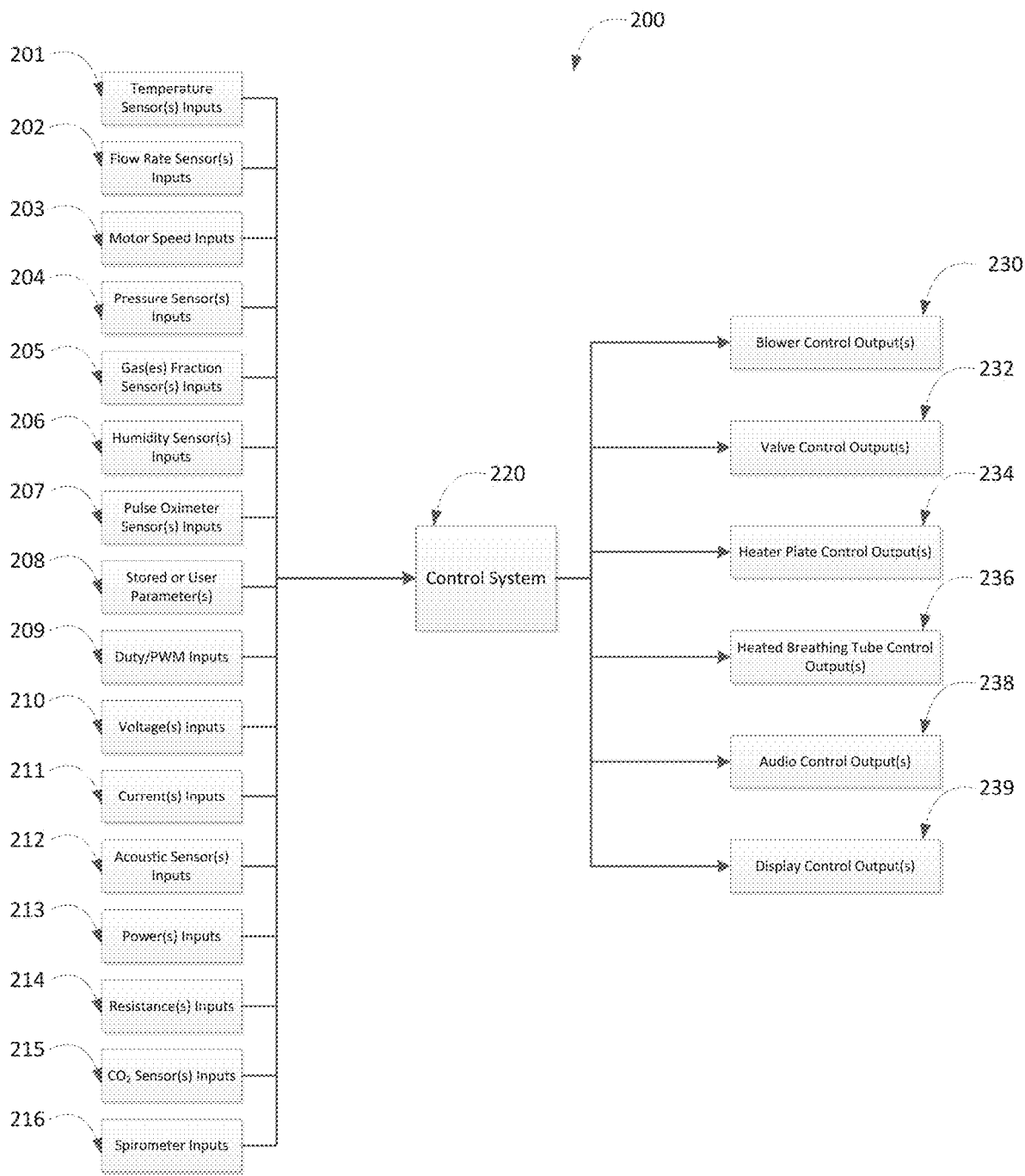
FIG. 2A illustrates an example block diagram of a control system interacting with and/or providing control and direction to components of a respiratory assistance system.

FIG. 2A illustrates a block diagram 200 of an example control system 220 that can detect patient conditions and control operation of the flow therapy apparatus including the gas source. The control system 220 can manage a flow rate of the gas flowing through the flow therapy apparatus as it is delivered to a patient. For example, the control system 220 can increase or decrease the flow rate by controlling an output of motor speed of the blower 230 (hereinafter also referred to as a "blower motor") or an output of a valve 232 in a blender. The control system 220 can automatically determine a set value or a personalized value of the flow rate for a particular patient as discussed below. The flow rate can be optimized by the control system 220 to improve patient comfort and therapy.

The control system 220 can also generate audio and/or display/visual outputs 238, 239. For example, the flow therapy apparatus can include a display 308 and/or a speaker. The display 308 can indicate to the physicians any warnings or alarms generated by the control system 220. The display 308 can also indicate control parameters that can be adjusted by the physicians. For example, the control system 220 can automatically recommend a flow rate for a particular patient. The control system 220 can also determine a respiratory state of the patient, including but not limited to generating a respiratory rate of the patient, and send it to the display.

The control system 220 can change heater control outputs to control one or more of the heating elements (for example, to maintain a temperature set point of the gas delivered to the patient). The control system 220 can also change the operation or duty cycle of the heating elements. The heater control outputs can include heater plate control output(s) 234 and heated breathing tube control output(s) 236.

The control system 220 can determine the outputs 230-239 based on one or more received inputs 201-216. The inputs 201-216 can correspond to sensor measurements received automatically by the controller 300 (shown in FIG. 2B). The control system 220 can receive sensor inputs including but not limited to temperature sensor(s) inputs 201, flow rate sensor(s) inputs 202, motor speed inputs 203, pressure sensor(s) inputs 204, gas(s) fraction sensor(s) inputs 205, humidity sensor(s) inputs 206, pulse oximeter (for example, $SpO_2$) sensor(s) inputs 207, stored or user parameter(s) 208, duty cycle or pulse width modulation (PWM) inputs 209, voltage(s) inputs 210, current(s) inputs 211, acoustic sensor(s) inputs 212, power(s) inputs 213, resistance(s) inputs 214, $CO_2$ sensor(s) inputs 215, and/or spirometer inputs 216. The control system 220 can receive inputs from the user or stored parameter values in a memory 304 (shown in FIG. 2B). The control system 220 can dynamically adjust flow rate for a patient over the time of their therapy. The control system 220 can continuously detect system parameters and patient parameters. A person of ordinary skill in the art will appreciate based on the disclosure herein that any other suitable inputs and/or outputs can be used with the control system 220.

Figure 2B:
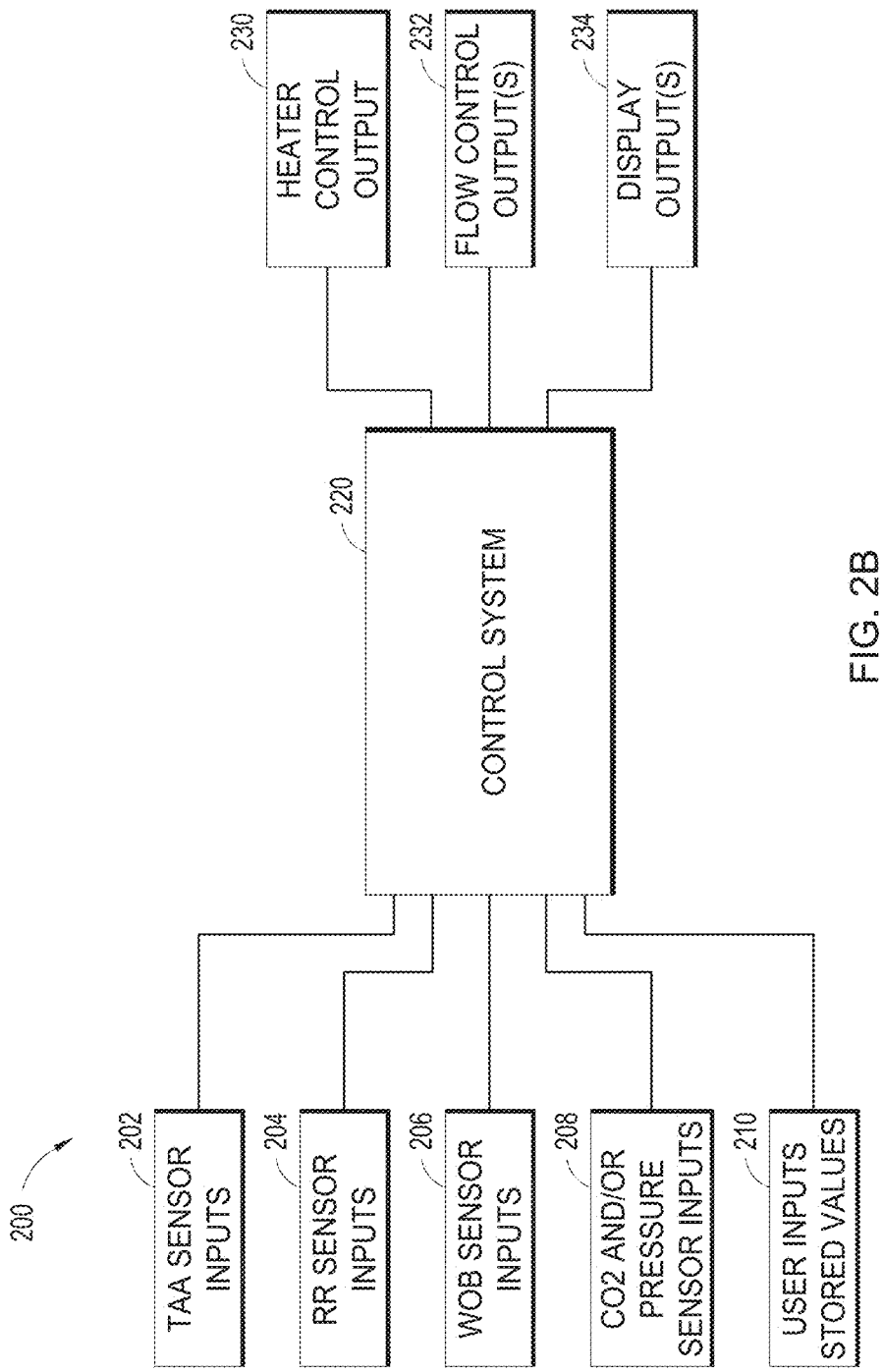
FIG. 2B illustrates an example block diagram of a control system interacting with and/or providing control and direction to components of a respiratory assistance system.

As illustrated in FIG. 2B, the control system 220 can receive inputs from multiple components of the flow therapy apparatus, such as thoraco-abdominal asynchrony (TAA) sensor inputs 202, respiratory sensor inputs 204, work of breathing (WOB) sensor inputs 206, CO2 and/or pressure sensor inputs 208, user inputs and/or stored values 210. Not all of the inputs 202-210 shown in FIG. 2A may be present. The control system 220 in FIG. 2B can output based on the inputs 202-210 heater control output 230, flow control output(s) 232, and display/audio output(s) 234. The inputs 202 to 210 and the outputs 230 to 234 may not necessarily be present. For example, the control system 220 may only receive the EMG input 206 and generate a flow control measurement 232. Depending on the configuration, some of the components corresponding to the inputs may not be included in the flow therapy apparatus. Lack of input itself can be used by the control system 220 to determine the input or system conditions.

Controller

The control system 220 can include programming instructions for detection of input conditions and control of output conditions. The programming instructions can be stored in a memory 304 of the controller 300 as shown in FIG. 2B. The programming instructions can correspond to the methods, processes and functions described herein. The control system 220 can be executed by one or more hardware processors 302 of the controller 300. The programming instructions can be implemented in C, C++, JAVA, or any other suitable programming languages. Some or all of the portions of the control system 220 can be implemented in application specific circuitry 306 such as ASICs and FPGAs.

Figure 2C:
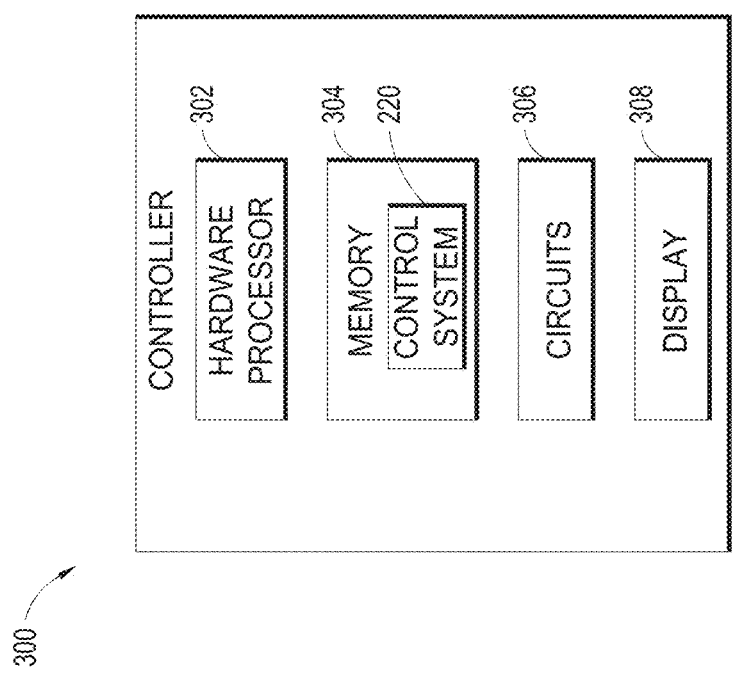
FIG. 2C illustrates a block diagram of an example controller.

FIG. 2C illustrates a block diagram of an example controller 300. The controller can include a hardware processor 302 that can execute the instructions stored in a memory 304. The control system 220 can be stored as programming instructions in the memory 304. The controller can also include circuits 306 for receiving sensor signals. The controller can further include a display 308 for transmitting status of the patient and the respiratory assistance system. The display 308 can also show warnings. The controller can also receive user inputs via the user interface such as the display 308. The user interface may alternatively or additionally comprise buttons or a dial.

Motor/Sensor Module

Figure 3:
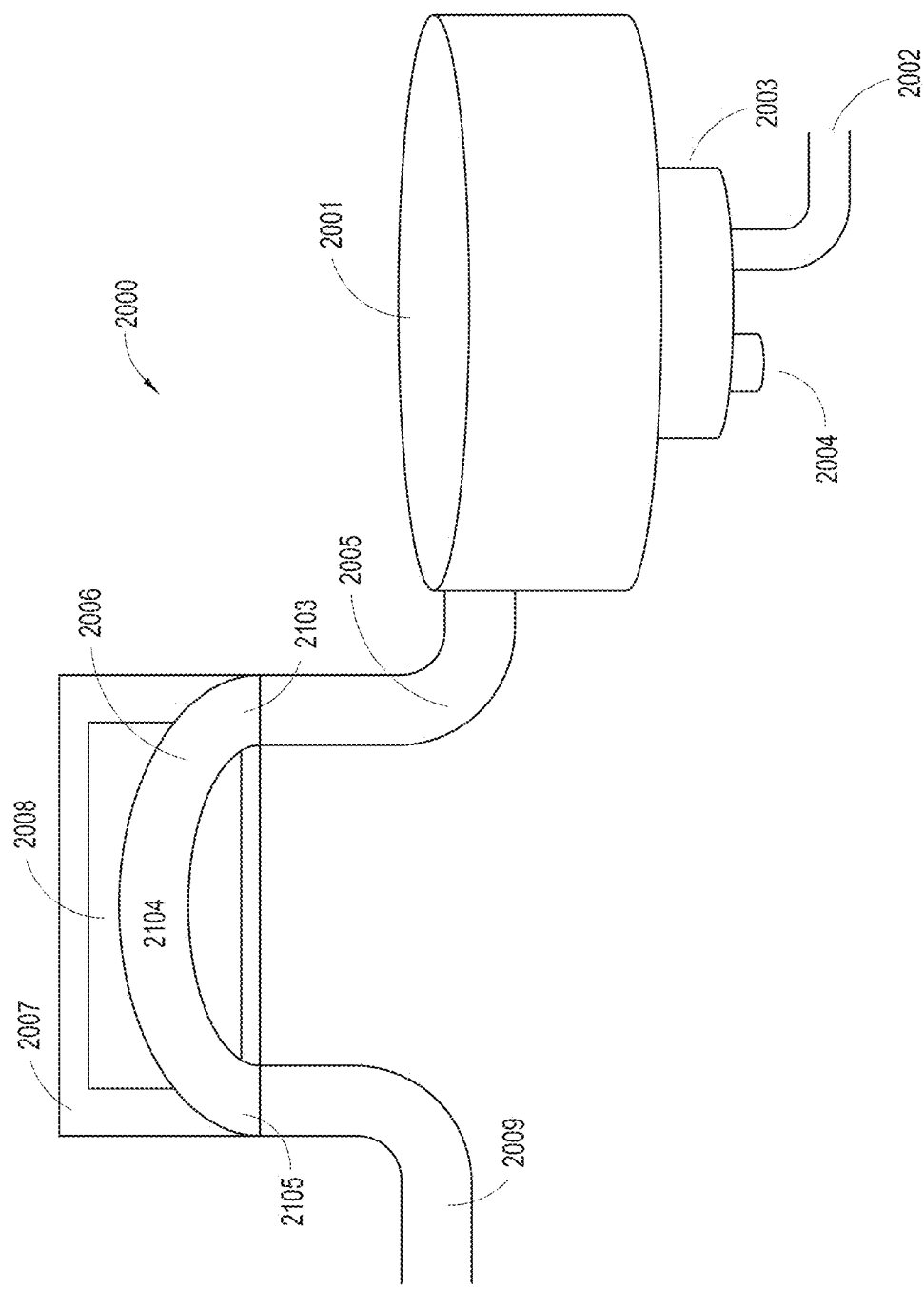
FIG. 3 illustrates a block diagram of an example motor/sensor module.

FIG. 3 illustrates a block diagram of a motor/sensor module 2000 which may be used as part of flow therapy apparatus. The motor/sensor module comprises a blower 2001, which entrains room air to deliver to a patient. The blower 2001 can be a centrifugal blower.

Room air enters a room air inlet 2002, which enters the blower 2001 through an inlet port 2003. The inlet port 2003 can comprise a valve 2004 through which a pressurized gas may enter the blower 2001. The valve 2004 can control a flow of oxygen into the blower 2001. The valve 2004 can be any type of valve, including a proportional valve or a binary valve. The inlet port can include no valves.

The blower 2001 can operate at a motor speed of greater than 1,000 RPM and less than 30,000 RPM, greater than 2,000 RPM and less than 25,000 RPM, greater than 20,000 RPM and less than 24,000 RPM, or between any of the foregoing values. Operation of the blower 2001 mixes the gases entering the blower 2001 through the inlet port 2003. Using the blower 2001 as the mixer can decrease the pressure drop that would otherwise occur in a system with a separate mixer, such as a static mixer comprising baffles, because mixing requires energy whereas the blower imparts energy.

The mixed air exits the blower 2001 through a conduit 2005 and enters the flow path 2006 in the measuring chamber 2007. A circuit board with sensors 2008 is positioned in the measuring chamber 2007 such that the circuit board is immersed in the gas flow. The sensors 2008 on the circuit board are positioned within the gas flow to measure gas properties within the flow. After passing through the flow path 2006 in the measuring chamber 2007, the gases exit 2009 to the liquid chamber 300.

Positioning sensors 2008 downstream of both the combined blower and mixer 2001 can increase accuracy of measurements, such as the measurement of gas fraction concentration, including oxygen concentration, over systems that position the sensors upstream of the blower and/or the mixer. Such a positioning can give a repeatable flow profile. Further, positioning the sensors downstream of the combined blower and mixer avoids the pressure drop that would otherwise occur, as where sensing occurs prior to the blower, a separate mixer, such as a static mixer with baffles, is required between the inlet and the sensing system. The mixer introduces a pressure drop across the mixer. Positioning the sensing after the blower allows the blower to be a mixer, and while a static mixer would lower pressure, in contrast, a blower increases pressure. Also, immersing the circuit board and sensors 2008 in the flow path increases the accuracy of measurements because the sensors being immersed in the flow means they are more likely to be the same temperature as the gas flow and therefore provide a better representation of the gas characteristics.

Measuring Chamber

As illustrated in FIG. 3, the measuring chamber 2007 can be positioned downstream of the blower 2001 within the motor/sensor module 2000. The measuring chamber 2007 comprises a flow path 2006 and is designed to hold the circuit board and the one or more sensors 2008.

Gas flows can experience pressure drops during passage through a flow therapy apparatus, which dissipates energy and in turn can affect the ability of the system to reach specific flow rates. Pressure losses can occur due to friction in straight sections of a flow path, or from deviations from a straight path, such as bends, valves, contractions, or expansions in the path.

The flow path 2006 has a curved shape. The gas flow enters at an entrance 2103, flows along a curved flow path 2104, and exits on the opposite side of the flow path 2105. The entrance and exit may be positioned in vertically opposed directions, and the gas flow may enter the path in a vertical upwards direction, then curve around to a horizontal direction, and then curve around to a vertical upwards direction again. The flow path may have no sharp turns. The flow path may have curved ends with a straighter middle section. The flow path can maintain a constant cross-section shape throughout the length of the flow path. The flow path can taper inward slightly from the first end of the flow path, and widens again to the second end of the flow path, which can speed up the flow for better accuracy, stability and reproducibility in measurements. The surface of the flow path can be lined with a surface modifier/lubricant to reduce friction within the flow path. A curved flow path shape can reduce a gas flow's pressure drop without reducing the sensitivity of flow measurements by partially coinciding the measuring region with the flow path. A number of different flow path configurations could be used. Additional examples of possible flow path configurations are disclosed in U.S. Provisional Application Ser. No. 62/262,325, referenced herein.

Adjusting Flow Based Upon Breath Cycle

In order to better assist a patient's breathing, it may be beneficial to be able to adjust the operation of a flow therapy apparatus based upon the patient's breath cycle. For example, as a patient inhales and exhales, a flow rate of air provided by the flow therapy apparatus may be adjusted. The flow rate can be adjusted based upon the patient's inspiration or expiration. For example, the flow rate may be increased during the patient's inspiration, and decreased during the patient's expiration. The flow rate may be adjusted during a patient's inspiration (for example, increased during inspiration), with no adjustment during the patient's expiration, or vice versa. Inspiration and expiration may also be referred to as inhalation and exhalation.

A patient's breathing cycle may be represented as a waveform comprising alternating exhale and inhale phases.

By determining and monitoring a patient's breath cycle waveform, operations of the flow therapy apparatus can be modified based upon the patient's breath cycle. For example, the flow therapy apparatus may be configured to control a gas flow using a periodic waveform, which may be adjusted based upon the patient's measured breath cycle waveform.

Figure 4:
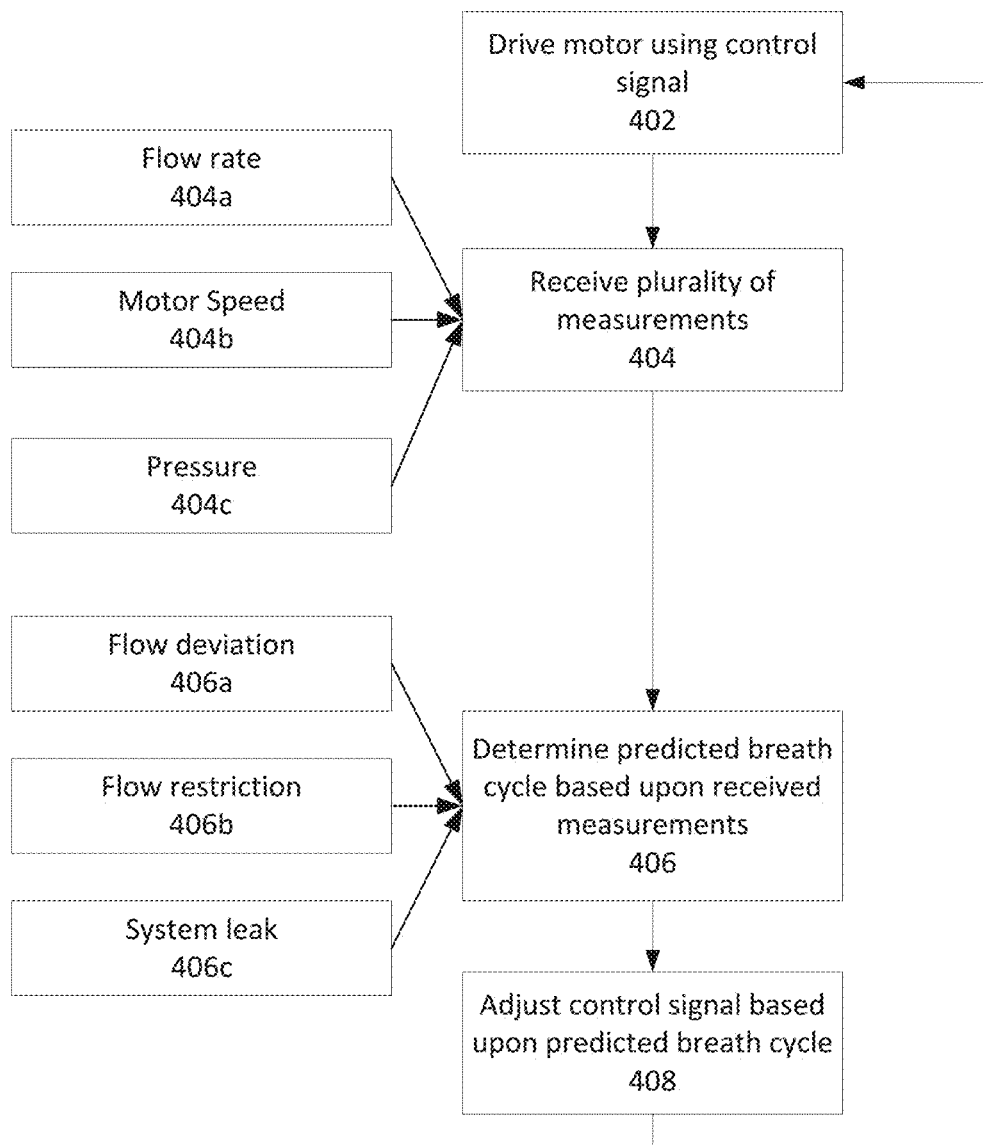
FIG. 4 illustrates a flowchart of an example process for adjusting the operation of a flow therapy apparatus

FIG. 4 illustrates a flowchart of an example process for adjusting the operation of a flow therapy apparatus. At block 402, a control signal is used to drive a blower motor associated with the flow therapy apparatus (for example, flow generator 11 as illustrated in FIG. 1 or blower 2001 illustrated in FIG. 3). The blower motor may be used to generate an air flow in order to assist the respiration of a patient. The control signal may comprise an initial waveform. The initial waveform may comprise a default waveform, or be based upon one or more measurements associated with the patient.

At block 404, a plurality of measurements are received that may be used to determine a breathing cycle of the patient. These may include a flow rate 404a, a motor speed 404b, a pressure 404c, and/or the like. Each of these types of measurements will be described in greater detail below.

At block 406, the received measurements are used to determine a predicted breath cycle of the patient. The predicted breath cycle of the patient may be determined using one or more different techniques, such as flow deviation 406a, flow restriction 406b, system leak 406c, and/or the like. Each of these different techniques will be described in greater detail below.

At block 408, the control signal to the blower motor is adjusted based upon the predicted breath cycle. For example, the control signal may be adjusted so that the flow rate is increased as the patient inhales, and decreased as the patient exhales. The control signal may be configured to be a phase-locked loop with the predicted breath cycle. Each of these implementations will be described in greater detail below.

The process may then return to block 402, where the adjusted control signal is used to drive the blower motor to produce an air flow for the patient.

Measuring System Parameters

As discussed, a patient's breath cycle can be determined based at least in part upon a plurality of different measurements, such as a measured flow, a measured motor speed, a measured pressure, or a combination thereof.

a) Flow

Flow refers to a flow of gas through the system (for example, from a blower motor or other flow generator to a patient). A flow rate may be measured using one or more flow sensors. For example, the flow rate may be measured using a heated temperature sensing element. A heated temperature sensing element can comprise a heated temperature sensing element, hot wire anemometer, such as a platinum wire or heated thermistor, and/or a negative temperature coefficient (NTC) thermistor. Other non-limiting examples of the heated temperature sensing element include glass or epoxy-encapsulated or non-encapsulated thermistors. The heated temperature sensing element is configured to measure flow rate of the gases.

Flow rate may be measured using a fast response-time flow sensor such as an ultrasonic sensor assembly comprising first and second ultrasonic transducers. The one or more sensors may be located in proximity to a flow path, such as that illustrated in FIG. 3. An example of measuring flow using ultrasonic transducers along a portion of the flow path is discloses in U.S. Provisional Application Ser. No. 62/262,325, referenced herein. Specifically, a first ultrasonic transducer can be at a downstream portion of a flow path in the measuring chamber described above and a second ultrasonic transducer can be at an upstream portion of the flow path in the measuring chamber described above. The first and second ultrasonic transducers can each transmit toward and receive from each other ultrasonic signals. The controller of the respiratory apparatus can determine one or more characteristics of the gas flow, including but not limited to the flow rate, based on time of flight measurements between the first and second ultrasonic transducers. Flow rate may also be measured using one or more ultrasonic transmitters and one or more ultrasonic receivers, such as microphones. The one or more ultrasonic transmitters can transmit, along an acoustic path, ultrasonic signals. The one or more ultrasonic receivers can be positioned along the acoustic path and receive the ultrasonic signals. The controller of the respiratory apparatus can determine one or more characteristics of the gas flow, including but not limited to the flow rate, based on time of flight measurements between the one or more ultrasonic transmitters and receivers.

Because the flow rate of the system may fluctuate as the patient inhales and exhales, it is important to be able to measure flow rate quickly and with accuracy. The flow rate may be measured using a combination of two or more different sensors. For example, a first type of sensor may be able to measure flow rate with better short-term or local accuracy (for example, detecting rapid, breath by breath changes in flow rate) but may have poorer long-term accuracy (for example, due to the accumulation of small errors), while a second type of sensor may be able to measure flow rate with poorer local accuracy (for example, due to local noise) but better average accuracy. Output readings from both the first and second types of sensors may be combined to determine a more accurate flow measurement. For example, a previously determined flow rate and one or more outputs from the second type of sensor can be used to determine a predicted current flow rate. The predicted current flow rate may then be updated using one or more outputs from the first type of sensor, in order to calculate a final flow rate. The first type of sensor may comprise an ultrasonic sensor assembly, while the second type of sensor may comprise a heated temperature sensing element.

Figure 5:
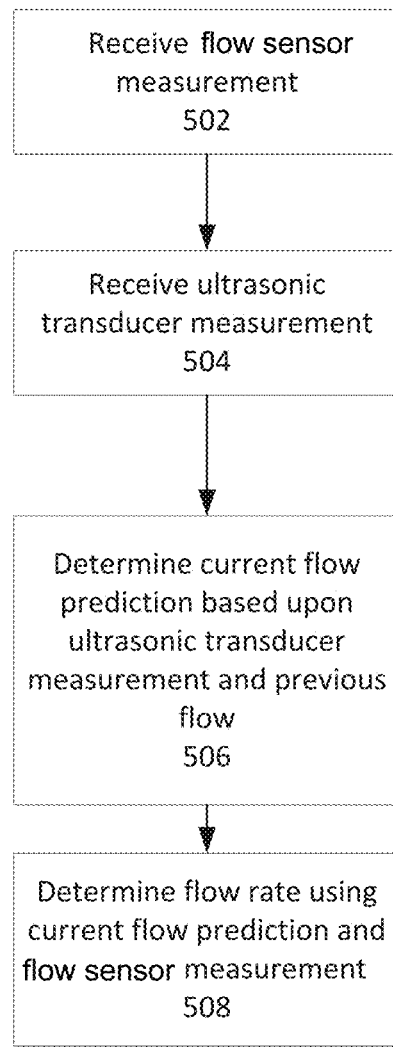
FIG. 5 illustrates a flowchart of an example process for determining a flow rate.

FIG. 5 illustrates a flowchart of an example process for determining a flow rate. At block 502, a first flow rate measurement is received from a first flow sensor, such as a heated temperature sensing element sensor. At block 504, a second flow rate measurement is received from an ultrasonic sensor assembly as described above.

At block 506, a current flow prediction is determined, based upon the second flow rate measurement and a previous flow rate measurement. At block 508, a flow rate is determined using the current flow prediction and the first flow rate measurement. By utilizing both a heated temperature sensing element sensor and ultrasonic transducers, the shortcomings of both types of sensors may be alleviated, allowing for flow rate to be measured quickly and accurately.

Measurements from different types of sensors may be combined in different ways. For example, measurements from one or more ultrasonic transducers can be read directly, while heated temperature sensing element measurements are filtered in to provide underlying corrections to the ultrasonic flow computation (for example, by using the heated temperature sensing element, which has better long-term accuracy, to correct the measurements of the ultrasonic transducers, which exhibit faster response times).

b) Motor Speed

One or more sensors (for example, Hall-effect sensors) may be used to measure a motor speed of the blower motor. The blower motor may comprise a brushless DC motor, from which motor speed can be measured without the use of separate sensors. For example, during operation of a brushless DC motor, back-EMF can be measured from the non-energized windings of the motor, from which a motor position can be determined, which can in turn be used to calculate a motor speed. In addition, a motor driver may be used to measure motor current, which can be used with the measured motor speed to calculate a motor torque. The blower motor may comprise a low inertia motor.

c) Pressure

System pressure may be determined using one or more pressure sensors. The one or more pressure sensors can be one or more gauge pressure sensors or one or more absolute pressure sensors. The one or more pressure sensors may be anywhere in the system, but at least one pressure sensor can be positioned in the flow path within the main housing of the breathing apparatus. One or more motor parameters may be used to determine a system pressure, without the need for a separate pressure sensor. A pressure sensor may be used to confirm the system pressure determined from the parameters of the motor.

Using motor parameters to calculate system pressure may have good short term accuracy, but may have poorer long-term average accuracy in comparison to using a separate pressure sensor. As such, outputs from the pressure sensor and motor parameters may be used together to determine an accurate system pressure measurement (for example, using one or more of the techniques described above with regards to flow rate measurement).

Determining Breath Cycle a) Flow Deviation

A breath cycle of the patient can be determined by observing deviations of the flow rate of the system $Q$ relative to an average or set-point flow rate value $\overline{Q}$. For example, flow rate may tend to increase in response to a patient inhaling, and decrease in response to the patient exhaling. However, because the speed of the motor may also vary, it may be difficult to determine what portion of the deviation is due to changes in the motor speed, and what portion is due to the patient's breath cycle.

b) Restriction

Flow restriction may be used to determine a patient's breath cycle. In general, a breathing system as a whole will have some resistance to flow (also referred to as "Restriction" or R), which can be used to indicate a relationship between change in pressure p of the system and the flow of the system squared ($Q^2$), as shown in the following equation.

$$p = RQ^2$$

Thus, restriction R can be approximated as:

$$R = \frac{p}{Q^2}$$

The restriction R may vary as the patient inhales and exhales. Smaller values of R represent larger restrictions (for example, when the patient exhales).

In addition, pressure p may also be approximated as a function of the motor speed, as shown in the following equation:

$$p = k_m \omega^2$$

where $\omega$ corresponds to motor speed and $k_m$ corresponds to a constant. As such, restriction R can be approximated as:

$$R = k_m \left(\frac{\omega}{Q}\right)^2$$

As such, using changing values of R as an indication of a patient's breath cycle, the patient's breath cycle may be determined based upon a measured flow rate $Q$ and a measured motor speed $\omega$. One or more pressure measurements may be used to calculate a value of the constant $k_m$, or a value of $k_m$ may be assumed.

Pressure drop due to patient breath cycle (inhaling/exhaling) and pressure drop due to the other factors (also referred to as system pressure drop) can be summed, as shown in the following equation:

$$k_m \omega^2 = k_c Q^2 + RQ^2$$

$$R = k_m \left(\frac{\omega}{Q}\right)^2 - k_c$$

where $k_c$ corresponds to a constant associated with system pressure drop. Detection of a patient's breath cycle is based upon detecting deviations of R (for example, deviations from an average value $\overline{R}$), instead of the magnitude of R. As such, the constant $k_c$ can be negligible. The values of $\overline{R}$ may be tracked as a moving average, in order to compensate for deviations in the restriction (for example, due to an irregular breath, movement of the cannula, and/or the like) and provide a smoother waveform.

c) System Leak

A flow of air generated by a blower can comprise a first portion flowing to a patient's lungs and a second portion leaked by the system, referred to as "leak flow." This may be expressed by the following equation:

$$Q = Q_p + Q_l$$

where $Q_p$ corresponds to patient flow and $Q_l$ corresponds to leak flow.

In addition, the pressure at the cannula may be referred to as "leak pressure drop." A total blower pressure of the system may be approximated as a sum of a system pressure drop and leak pressure drop, which can be expressed as:

$$k_m \omega^2 = k_c Q^2 + k_l Q_l^2$$

where $k_l$ corresponds to a leakage constant. In a closed or sealed system, $k_l$ would be a constant. In non-sealed systems, $k_l$ may vary with time as the patient breathes, but may be treated as substantially constant over a particular breath cycle. $k_l$ characterizes the "system leak."

As such, leak flow can be approximated as:

$$Q_l = \sqrt{\frac{k_m \omega^2 - k_c Q^2}{k_l}}$$

The pressure at the cannula can be approximated as $k_l Q_l^2$ (leak pressure only), and the patient's lung flow can be approximated as $Q_p = Q - Q_l$. As the patient's lung flow varies, the patient's breath cycle may be determined.

As described above, the variables $Q$, $Q_p$, $Q_l$, $k_m$, and $k_c$ can be measured, calculated, or estimated. In addition, $k_l$ can be estimated by knowing that the average flow into the patient's lungs will be approximately zero for purposes of delivering breath assistance. In other words, the following assumptions can be made: $\overline{Q_p} = 0$ and $\overline{Q_l} = \overline{Q}$. A difference in the amount of gases a patient inhales and exhales due to gas exchange (also referred to as "drift") may be calculated, allowing drift correction to be performed on the average flow. If a period T of the patient's breath is known, then the average leak of the system may be approximated by:

$$\overline{Q_l} = \frac{1}{T} \int_0^T Q_l \, dt = \frac{1}{T\sqrt{k_l}} \int_0^T \sqrt{k_m \omega^2 - k_c Q^2} \, dt = \overline{Q}$$

The equation above then can be used to compute $k_l$. If the period T is unknown, a time-weighted average may be used on a period of time where there is known to be a certain number of breath to approximate the period T.

Once the patient's breath cycle is determined (for example, using any of the techniques disclosed above), the control signal can be adjusted based upon the patient breath cycle. In addition, the breath cycle may be used to calculate a patient breath rate (for example, breaths per minute). The calculated breath rate may be displayed (for example, at display 308), stored, or transmitted.

Pressure Control in Sealed Systems

A pressure sensor reading can be available at the patient end or along a portion of the patient breathing conduit in a respiratory system with a sealed patient interface as described above. The pressure sensor reading can also be available from within the flow therapy apparatus. The pressure sensor can be placed anywhere in the flow path. A non-limiting example of a sealed patient interface is an NIV mask. NIV masks can be sealed against the patient's face, resulting in substantially no system leak. This makes it possible to measure the pressure of the gases delivered to the patient near or at the patient end. A pressure sensor can be positioned inside the NIV mask. The pressure sensor can be positioned at a location outside the patient's nares. The pressure sensor can be positioned in a manifold connecting the NIV mask to the patient breathing conduit, such as the patient breathing conduit 16 shown in FIG. 1.

Measurements from the pressure sensor located near or at the patient end, such as the pressure sensor in the NIV mask or along a portion of the patient breathing conduit, can allow control of the pressure delivered to the patient using some of the equations described above. Specifically, the pressure term, $RQ^2$, in the equation $k_m \omega^2 = k_c Q^2 + RQ^2$ can be replaced by the pressure sensor reading, P, to arrive at the following equation.

$$k_c = \frac{k_m \omega^2 - P}{Q^2}$$

For this equation, it can be assumed that $Q/\omega$ is approximately constant as the operation of the system does not change rapidly. This equation can be further rearranged, by multiplying both sides of the equation with a term $(Q/\omega)^2$, to arrive at an expression that more clearly shows how the pressure sensor reading, P, and/or the flow of the system, $Q$, can impact the motor speed, $\omega$.

$$\omega_s = \sqrt{\frac{P_s}{k_m - k_c \left(\frac{Q}{\omega}\right)^2}}$$

Based on this equation, the desired pressure of the system can be achieved by controlling the motor speed. If a desired or predetermined pressure of the system is known, the motor speed that is required to achieve the desired or predetermined pressure can be calculated. The controller can then control the pressure of the system by adjusting the motor speed in a sealed respiratory system.

Breath Cycle Enhancement

Once a patient's breath cycle has been determined, the control signal to the blower motor may be adjusted based upon the determined breath cycle, in order to better assist the respiration of the patient. For example, a flow therapy apparatus may assist the breath cycle of a patient by increasing air flow while the patient is inhaling, while decreasing flow while the patient is exhaling.

Figure 6A:
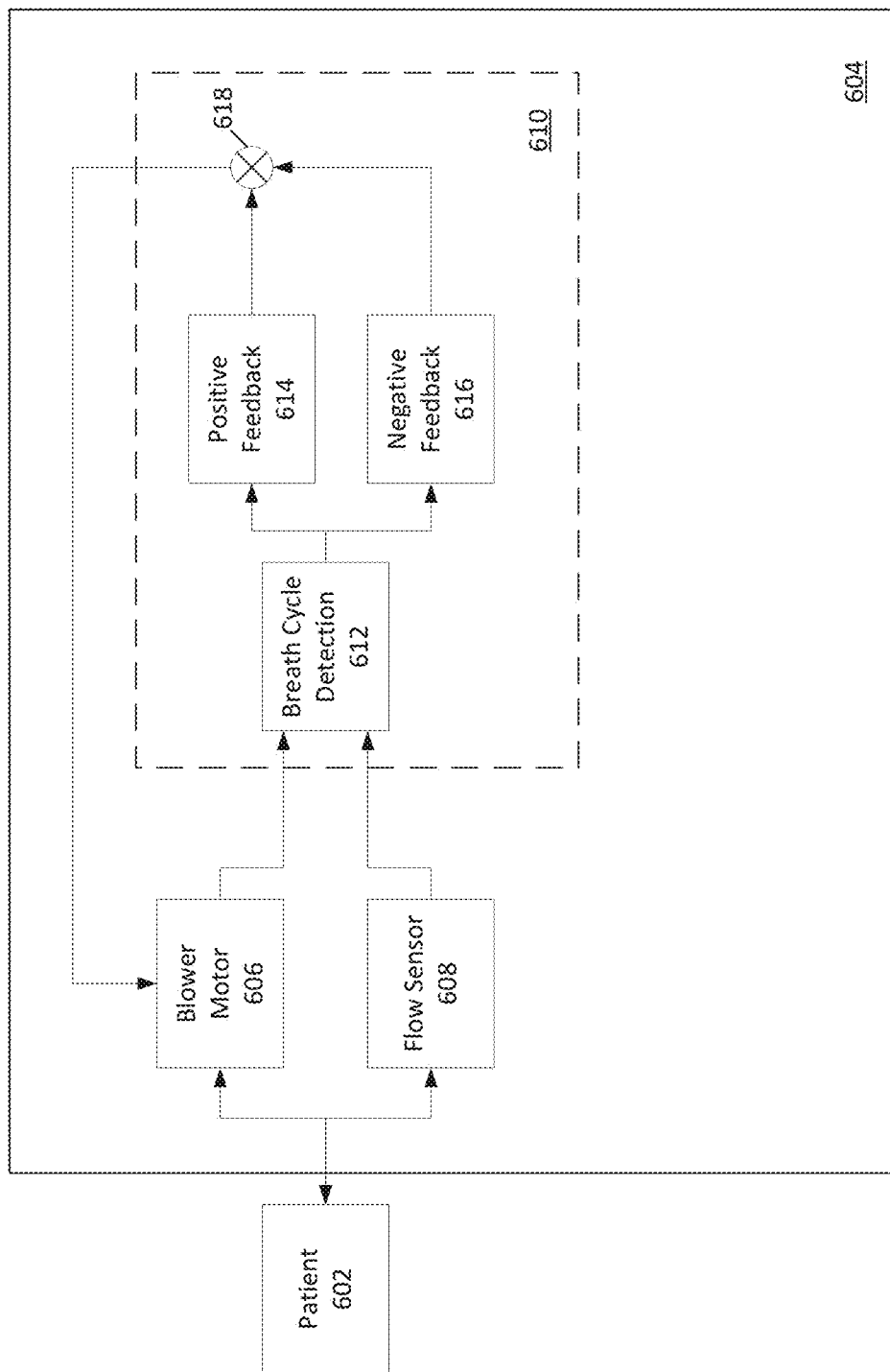
FIG. 6A illustrates a block diagram of an example system for performing breath cycle enhancement for a flow therapy apparatus.

FIG. 6A illustrates a block diagram of an example system for performing breath cycle enhancement for a flow therapy apparatus. As illustrated in FIG. 6A, a patient 602 is connected to a flow therapy apparatus 604. Breathing system apparatus 604 comprises a blower motor 606 or other type of flow generator, which may be used to provide an air flow to the patient 602.

During operation of the flow therapy apparatus 604, a plurality of measurements may be taken and transmitted to a control signal feedback module 610, in order to adjust a control signal to the blower motor 406 based upon a breath cycle of the patient 602. For example, parameters of the blower motor 406 may be used to measure a motor speed and/or a system pressure. A flow rate of the air flow may be monitored using one or more flow sensors 608. The flow sensors 408 may comprise two or more different types of sensors, such as a heated temperature sensing element and an ultrasonic sensor assembly. In addition, one or more additional sensors, such as pressure sensors (not shown) may be used to measure one or more additional measurements (for example, pressure).

The plurality of measurements (for example, motor speed, flow rate, and/or the like) may be used to determine a breath cycle of the patient at a breath cycle detection module 612. The determined breath cycle may be in the form of an alternating waveform (for example, a substantially sinusoidal waveform).

Once the breath cycle of the patient has been determined, it may be used to adjust the control signal to blower motor 606. For example, the calculated breath cycle waveform from the breath cycle detection module 612 may be subject to positive feedback 614 and/or negative feedback 616. Both positive feedback 614 and negative feedback 616 may be performed based upon the calculated breath cycle, and combined at 618 generate a control signal for blower motor 602.

Positive feedback 614 can function to work with the patient during the patient's breath cycle, by backing off the motor speed as the patient exhales, and/or increasing motor speed as the patient inhales. One or more scaling parameters may be used to increase/decrease the magnitude of the control signal controlling the speed of blower motor 406, based upon a determined magnitude of the patient's inhale/ exhale. For example, positive feedback for the blower motor control signal may be expressed as:

$$\omega = \overline{\omega} + k_p(R - \overline{R})$$

where ω corresponds to motor speed, R corresponds to a patient restriction, $\overline{\omega}$ and $\overline{R}$ correspond to their average or baseline values, and $k_p$ corresponds to a positive feedback parameter.

On the other hand, negative feedback 616 may be used to limit the positive feedback provided to the patient's breath cycle, by suppressing the change to the control signal as the patient inhales or exhales. For example, as the patient inhales, the motor speed of the blower motor may only be increased up to a certain limit, even as the magnitude of the patient's inspiration increases. Negative feedback 616 may optionally be used only when a magnitude of the patient's inhale or exhale exceeds a threshold level. Negative feedback may be provided during inspiration but not expiration, or vice versa.

Negative feedback may comprise limiting the positive feedback applied to the control signal to certain bounds. The negative feedback may comprise an explicit term, such as:

$$\omega = \overline{\omega} + k_p(R - \overline{R}) - k_n(R - \overline{R})^N$$

where the negative feedback parameters $k_n$ and N are set such that negative feedback is negligible when restriction deviation R-$\overline{R}$ is low (for example, close to zero), but starts to dominate positive feedback as deviation increases. An amount of positive or negative feedback (for example, the values of positive and negative feedback parameters $k_p$ and $k_n$) may be adjusted based upon the patient's breath cycle (for example, whether the patient is inhaling or exhaling).

Figure 7:
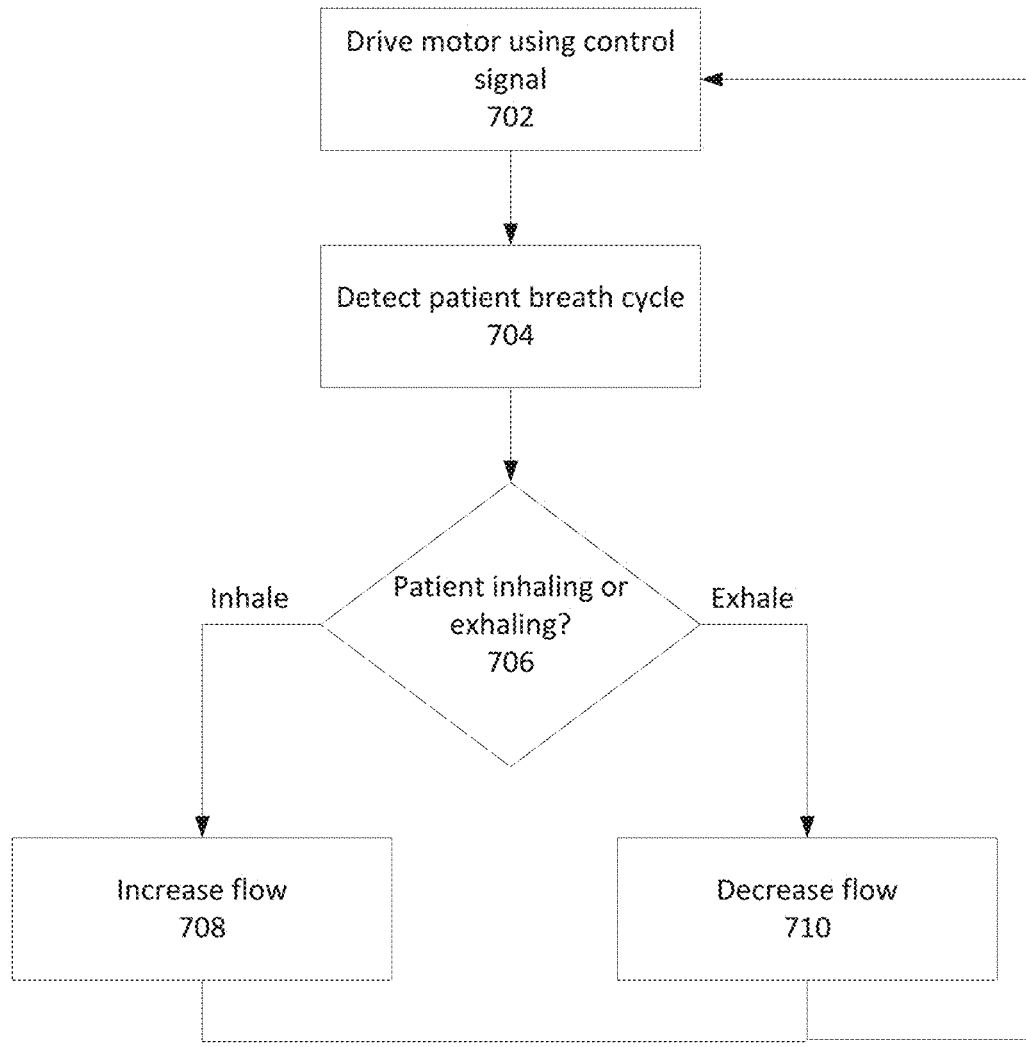
FIG. 7 illustrates a flowchart of an example process for assisting the breath cycle of a patient.

FIG. 7 illustrates a flowchart of an example process for assisting the breath cycle of a patient. At block 702, a blower motor associated with the flow therapy apparatus is driven using a control signal.

At block 704, a patient breath cycle is detected. Detecting the patient breath cycle may comprise receiving a plurality of measurements from one or more sensors, such as a flow rate measurement, a motor speed measurement, a pressure measurement, and/or the like. The received measurements may be used to determine the breath cycle of the patient, for example, using any of the techniques described above.

At block 706, a determination is made as to whether the patient is currently inhaling or exhaling. If the patient is inhaling, then at block 708, the control signal to the motor may be modified to increase air flow to the patient, potentially reducing the work of breathing needed to be done by the patient during inspiration. Work of breathing can be reduced due to the increased air flow. On the other hand, if the patient is exhaling, then at block 710, the control signal to the motor may be modified to decrease air flow to the patient. This may be beneficial for the patient as it lowers the work of breathing during expiration, due to the patient not having to breathe into an incoming flow of air. In addition, noise caused by collisions between the patient's exhaled gas and the incoming gas from the cannula may be reduced. Being able to adjust the air flow based upon patient inspiration/expiration may enhance the effects of high flow respiratory therapy. For example, as the patient will not have to breathe into an incoming air flow during expiration, a substantially higher flow rate may be delivered (for example, during inspiration) to provide greater dead space washout and/or $CO_2$ flushing.

An amount of increase or decrease in the airflow may be based upon a magnitude of inspiration/expiration by the patient. A combination of positive and negative feedback can be used to adjust the control signal. For example, positive feedback may be used to assist the patient's breathing by increasing motor speed when the patient is inhaling and decreasing motor speed when the patient is exhaling, based upon a magnitude of the patient's inspiration/expiration, while negative feedback may be used to bound or temper the positive feedback applied to the motor control signal. The process may then return to block 702, where motor is driven using the updated control signal, and the patient's breath cycle continues to be monitored.

While FIG. 7 illustrates feedback being implemented during both the inspiration and expiration phases of a patient's breath cycle, as discussed above, positive or negative feedback parameters may be adjusted based at least in part upon where the patient is at in the breath cycle (for example, whether the patient is inhaling or exhaling). For example, positive feedback may be implemented during inspiration but not during expiration. For example, a patient that attempts to lower their work when breathing using "pursed lip breathing" on expiration may benefit from being assisted with positive feedback for increasing flow rate during inspiration, but no positive feedback for decreasing flow rate during expiration. By not implementing positive feedback during expiration, expiration pressure and expiration time may be increased, which may be beneficial for certain patients.

Phase-Shifted Control Loop

In order to assist the breathing of the patient, the control signal for driving the blower motor can be configured to be a phase-locked loop with the sensed breath cycle of the patient, synchronizing the control signal with the patient's breath cycle.

Figure 6B:
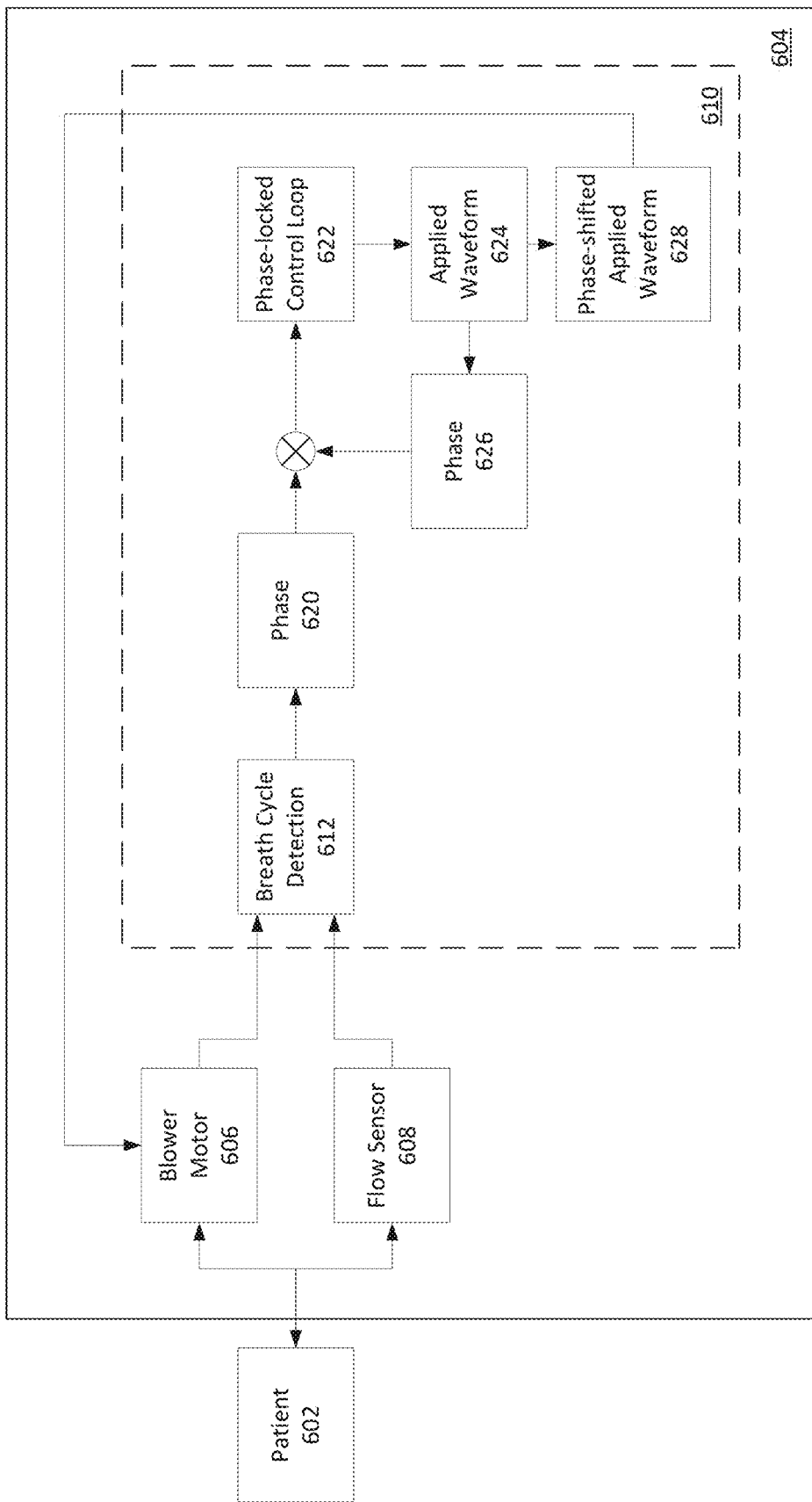
FIG. 6B illustrates a block diagram of an example system for implementing a phase-locked control loop for a flow therapy apparatus.

FIG. 6B illustrates a block diagram of a system for implementing a phase-locked control loop for a flow therapy apparatus. As illustrated in FIG. 6B, a patient 602 is connected to a flow therapy apparatus 404, similar to as illustrated in FIG. 6A. A blower motor 606 is configured to supply an air flow to the patient 602, in accordance with a received control signal. The control signal controlling the blower motor 606 may comprise an initial periodic waveform (for example, a default waveform, or a waveform based upon one or more patient measurements).

The blower motor 606 and flow sensor 608 may be configured to measure motor speed and flow rate, respectively, which may be received by a control signal feedback module 610, where a breath cycle of the patient may be determined at a breath cycle detection module 612. The breath cycle may comprise a waveform.

Figure 8:
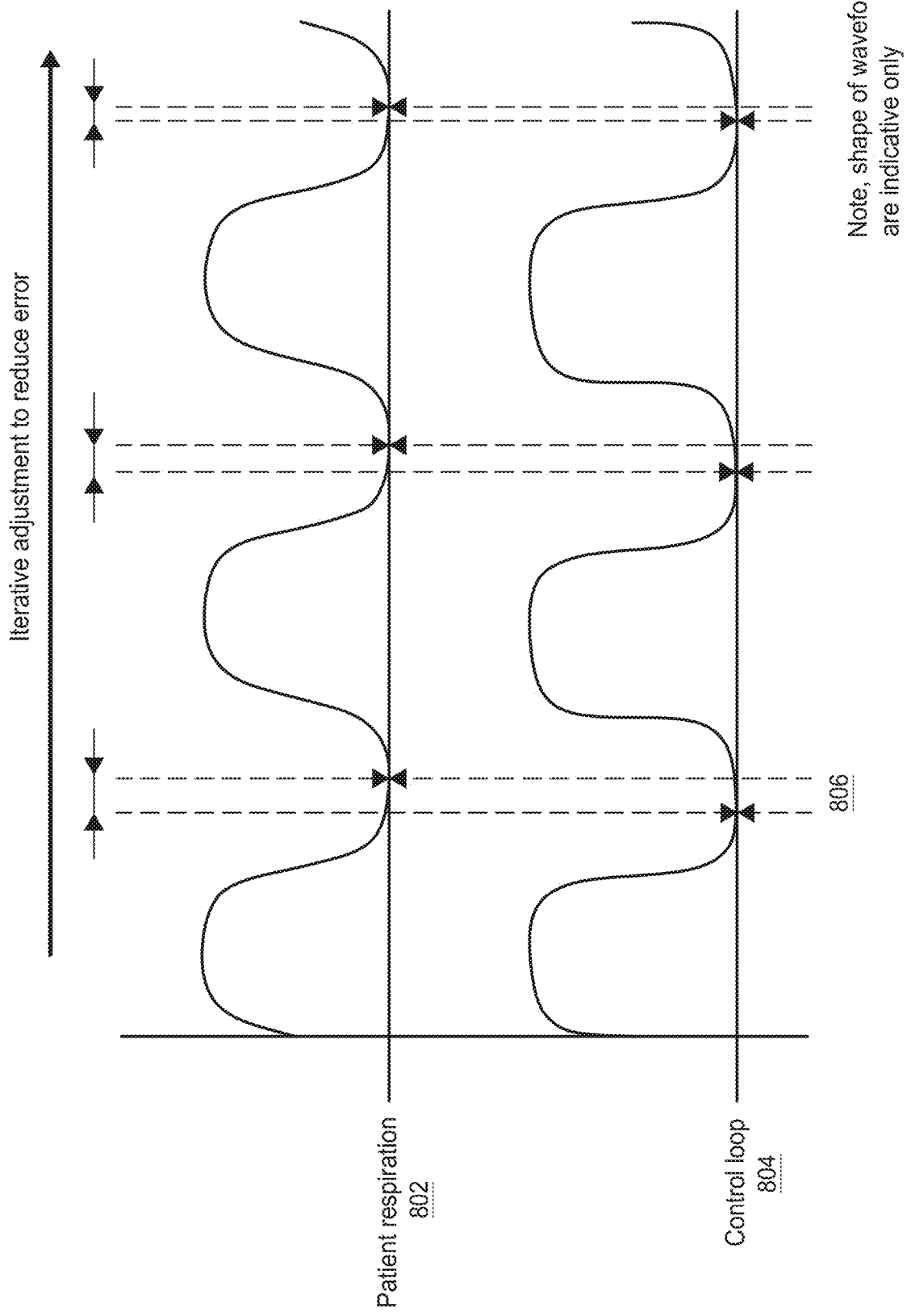
FIG. 8 illustrates an example chart of a patient's breath cycle waveform and a control signal waveform.

Using the determined breath cycle, a phase 620 of the patient's breath cycle waveform is determined, and compared with a phase 626 of an applied control signal waveform 624 to enter into a phase-locked control loop 622 that updates the phase of applied control signal waveform 624. As such, an error between the phase of the applied control signal waveform 624 and the breath cycle waveform can be iteratively reduced, causing the applied control signal waveform 624 to substantially match the patient's breath cycle in phase. For example, FIG. 8 illustrates an example chart of a patient's breath cycle waveform 802 and a control signal waveform 804. The phase of the control signal 804 is compared to that of the breath cycle 802 to determine a phase mismatch 806. The phase of the control signal 804 can be iteratively updated such that the phases of the control signal and the breath cycle will be substantially synchronized (for example, reducing phase mismatch 806). The phase of the control signal may be iteratively updated until the phase mismatch is within a threshold amount (for example, a set time, a phase percentage, and/or the like).

In addition, the control signal is phase-shifted to produce a phase-shifted applied waveform 628. The control signal waveform is phase-shifted in order to compensate for a delay between a signal to the blower motor and the patient receiving the resulting flow. The waveform may be phase-shifted in order to pre-empt a patient's breath cycle. For example, the control signal may be configured to increase the speed of the blower motor slightly before the patient begins to inhale, and to decrease the speed of the blower motor slightly before the patient begins to exhale. This provides a predictive system, rather than a strictly reactive system, such that it allows for a more comfortable breath transition as the patient inhales and exhales.

Figure 9:
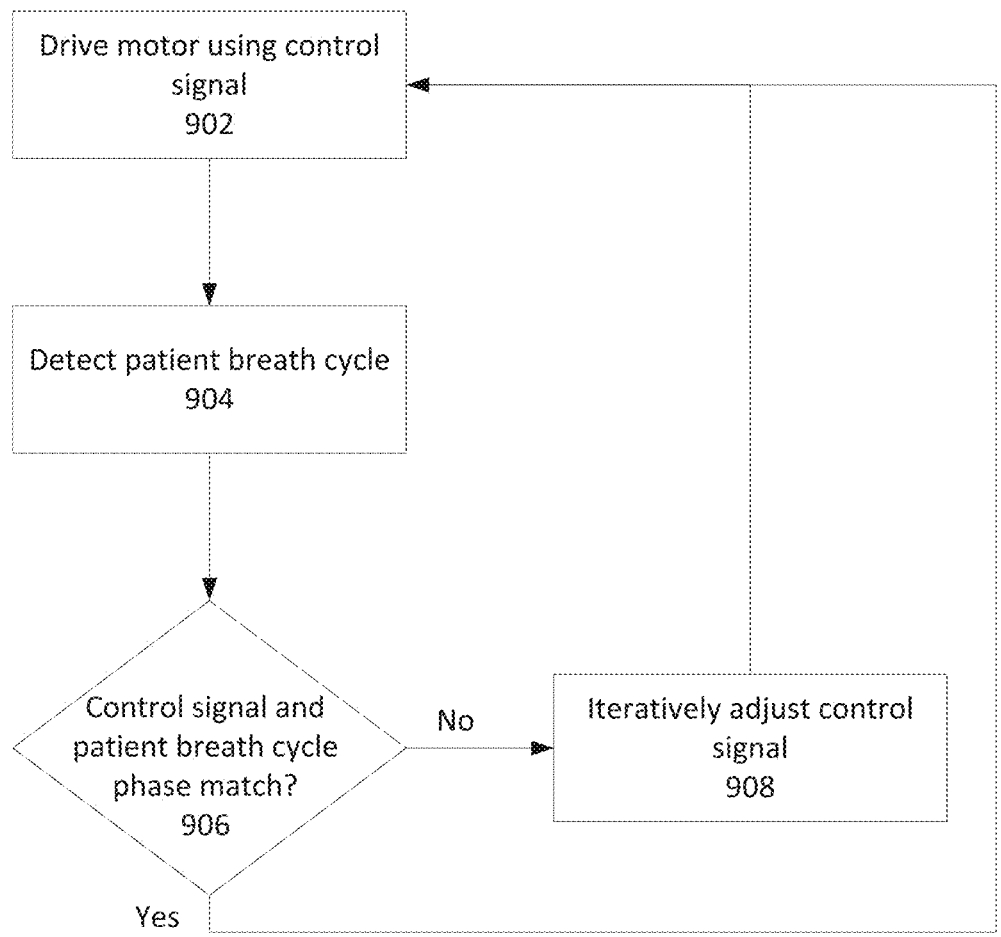
FIG. 9 illustrates a flowchart of an example process for implementing the control signal of the blower motor as a phase-locked loop with the sensed breath cycle of the patient.

FIG. 9 illustrates a flowchart of an example process for implementing the control signal of the blower motor as a phase-locked loop with the sensed breath cycle of the patient. At block 902, a blower motor associated with the flow therapy apparatus is driven using a control signal.

At block 904, a patient breath cycle is detected. Detecting the patient breath cycle may comprise receiving a plurality of measurements from one or more sensors, such as a flow rate measurement, a motor speed measurement, a pressure measurement, and/or the like. The received measurements may be used to determine the breath cycle of the patient, for example, using any of the techniques described above. In addition, a breath rate or frequency may be calculated based upon the determined breath cycle.

The controller can estimate the breath rate in a number of ways. The controller can estimate the breath rate when the controller starts initially and/or when the controller is running. The breath rate can be estimated by counting the zero-crossing of the breath signal of any of the types described herein. The breath rate can be estimated by taking the Fast Fourier Transform (FFT) of the breath signal and looking for a dominant frequency. The breath rate can be estimated by finding the zero-crossings or peaks of an autocorrelation of the breath signal.

Figure 14A:
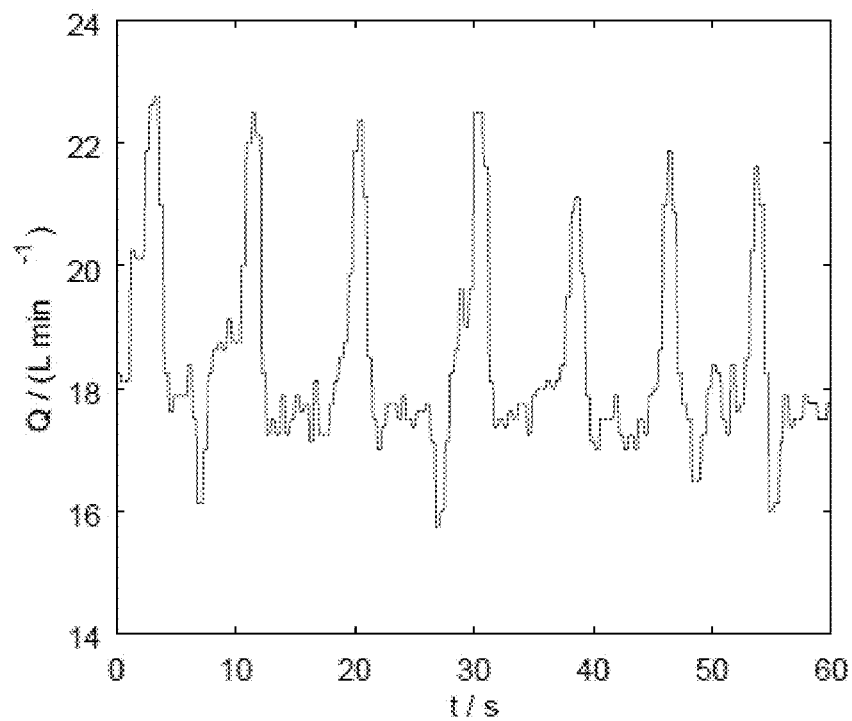
FIG. 14A illustrates an example chart of raw flow rate readings of a patient measured by the system.
Figure 14B:
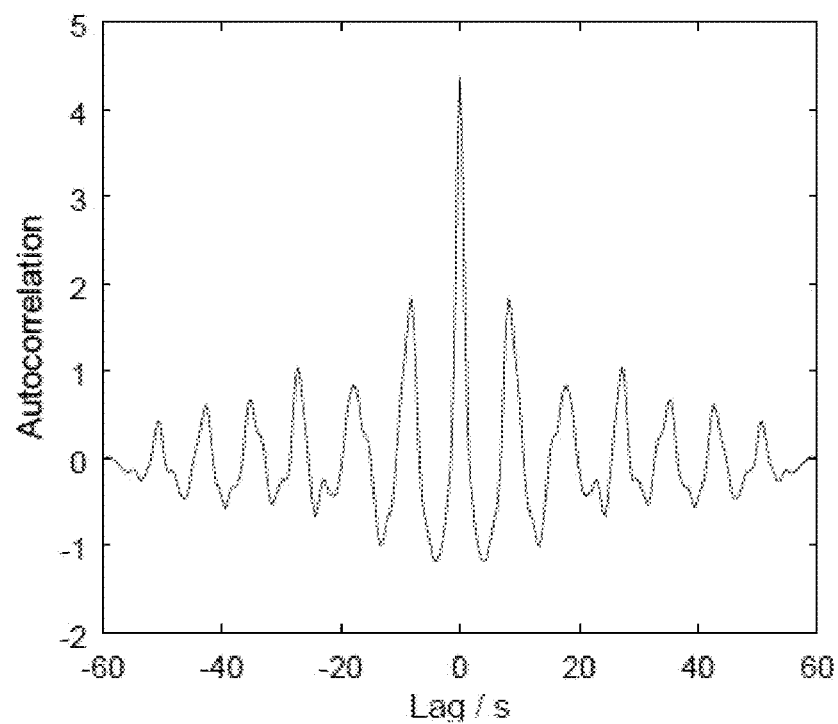
FIG. 14B illustrates an example chart of auto-correlation of the raw flow rate readings of FIG. 14A.

Autocorrelation can be a comparison of a signal with a delayed copy of itself as a function of delay. Autocorrelation can reveal repeating patterns concealed in a raw waveform of a signal, for example, by noise. Specifically, a plot of raw flow rate readings of a patient measured by the system with respect to time, such as the one shown in FIG. 14A, can be auto-correlated, such as shown in FIG. 14B. The peaks of the autocorrelation can be identified. The peaks can be at the estimated breath cycle, which can be used to estimate the patient's breath rate, also known as the respiratory rate. The breath cycle can also be determined by identifying the zero-crossings of the autocorrelation. The autocorrelation, particularly the first few cycles, can provide a more noise-robust estimate of the breath cycle than when working directly on the raw breath signal waveform. This is because edge detection can be unstable on the raw waveform due to noise.

Besides helping to determine the breath rate or frequency for implementing the control signal of the blower motor as a phase-locked loop, the respiratory rate information extracted from the autocorrelation can be used to provide compliance information. For example, the extracted respiratory rate information can be indicative of whether the patient is using the system correctly. The extracted respiratory rate information can be indicative of work of breathing.

At block 906, a determination is made as to whether a phase of the control signal matches a phase of a sensed patient breath cycle. This determination may be satisfied if the phase of the control signal is within a threshold amount or percentage of the phase of the sensed patient breath cycle. The phase difference between the control signal and the sensed patient waveform can be determined in a similar way as described above for estimating the breath rate. For example, the controller can perform a cross-correlation between the control signal and the sensed patient waveform and look for the peak in the cross-correlation. The peak can occur at or substantially at the time delay between the two waveforms.

If it is determined that the control signal phase does not match that of the sensed patient breath cycle, then at block 908, the phase of the control signal is iteratively adjusted to match that of the sensed patient breath cycle. The phase of the control signal may be adjusted by a predetermined amount, a predetermined percentage, a percentage or amount based upon a difference between the phase of the control signal and the phase of the sensed patient breath cycle, and/or the like. The process may then return to block 902, where the motor may continue to be driven by the control signal, and patient's breath cycle may continue to be monitored.

The amplitude of the control signal may be based upon one or more positive feedback or negative feedback parameters. For example, a magnitude of the patient's inspiration or expiration may be measured, and used to determine an amplitude of the control signal waveform using the positive and negative feedback parameters.

By implementing a phase-locked loop, synchrony between the control signal and the patient's breath cycle can be achieved to allow for a more comfortable breath transition as the patient inhales and exhales. When asynchrony is suspected, positive feedback may be reduced or eliminated. In such cases, the control signal may be configured to reduce a peak of the flow, or to cause the flow to be substantially constant, wherein the constant flow rate is lower than a flow rate when positive feedback is implemented. The reduction or elimination of positive feedback can reduce or eliminate potential discomfort to the patient due to positive feedback on the control signal. Once synchrony between the control signal and patient breath cycle is re-established, positive feedback may be recommenced or increased.

The control signal waveform may be introduced gradually as synchronisation is gained. For example, the amplitude of the control signal waveform may start at a lower value, such that the control signal waveform being slightly out of phase with the patient's breath cycle will not cause too much discomfort for the patient. As synchronization is gained, the amplitude of the control signal waveform may be increased.

The control signal waveform can be configured to achieve a targeted phase difference relative to the patient's breath cycle. For example, the control signal waveform may be phase-shifted a targeted amount relative to the breath cycle in order to compensate for a system delay, or to pre-empt the patient's breath cycle. These implementations are discussed in greater detail below.

Figure 10:
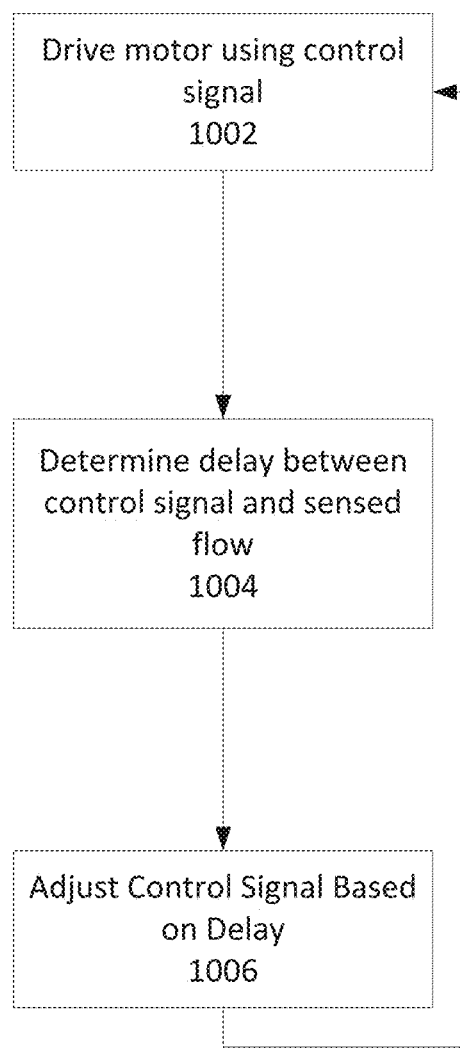
FIG. 10 illustrates a flowchart of an example process for phase-shifting a control signal to compensate for a system delay.

There may be a delay between when a control signal is delivered to a blower motor and when the resulting air flow produced by the blower motor can be sensed (due to, for example, motor speed up or slow down delay due to inertia, delays in sensing, and/or the like), and this is hereinafter referred to as system delay. The control signal may be phase-shifted in order to compensate for this system delay. FIG. 10 illustrates a flowchart of an example process for phase-shifting a control signal to compensate for a system delay. At block 1002, a blower motor associated with the flow therapy apparatus is driven using a control signal.

At block 1004, the resulting flow from the blower motor may be sensed using one or more sensors. The one or more sensors may comprise heated temperature sensing elements, ultrasonic sensors, and/or the like. Based upon the measured flow, a system delay is determined between when the control signal is received by the blower motor and when the resulting flow is sensed.

Figure 11:
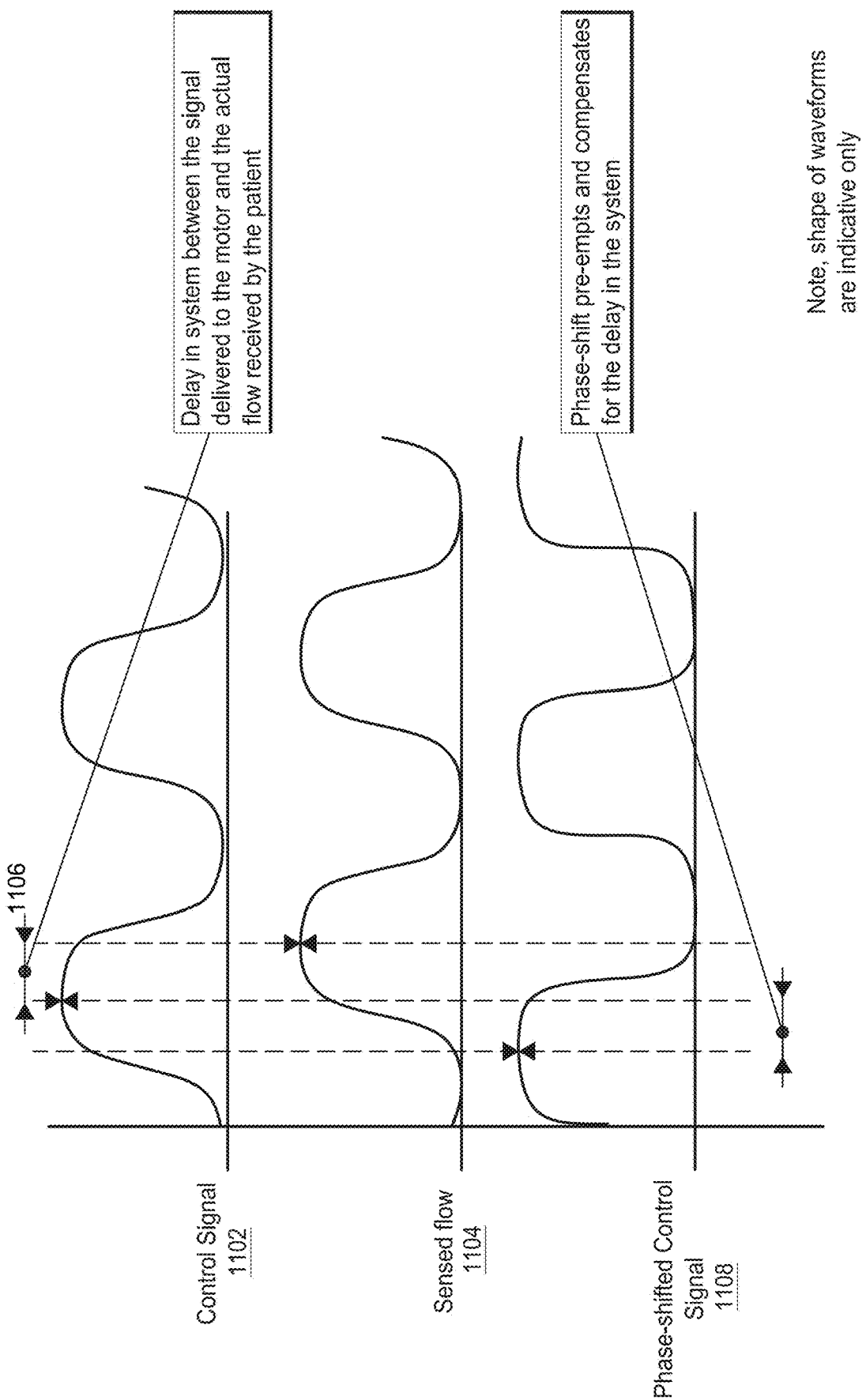
FIG. 11 shows charts illustrating updating a control signal to compensate for system delay.

At block 1006, the control signal is adjusted based upon the determined system delay. For example, FIG. 11 shows charts illustrating updating a control signal to compensate for system delays. A system delay 1106 between when a control signal 1102 is received by the motor and when the resulting flow 1104 is received by the patient is measured. The control signal may then be phase-shifted to form a phase-shifted control signal 1108, in order to compensate for the delay 1106.

Figure 12:
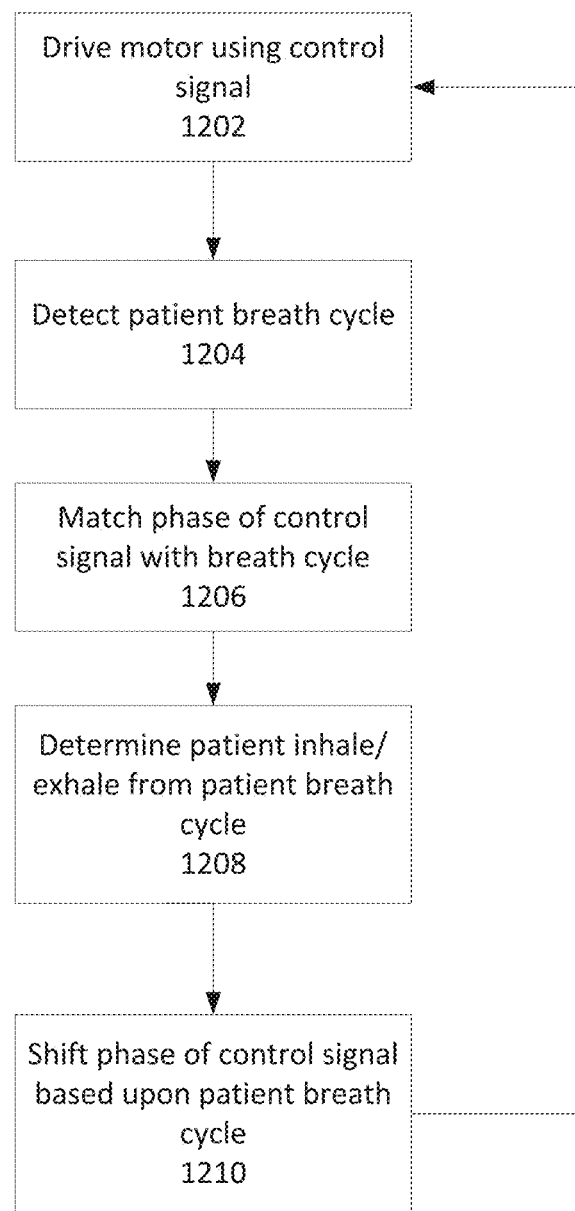
FIG. 12 illustrates a flowchart of an example process for configuring a phase-shifted control signal to pre-empt the patient's breath cycle waveform.

The control waveform may be further shifted such that it pre-empts the sensed breath cycle waveform. FIG. 12 illustrates a flowchart of an example process for configuring a phase-shifted control signal to pre-empt the patient's breath cycle waveform. At block 1202, a blower motor associated with the flow therapy apparatus is driven using a control signal.

At block 1204, a patient breath cycle is detected. Detecting the patient breath cycle may comprise receiving a plurality of measurements from one or more sensors, such as a flow rate measurement, a motor speed measurement, a pressure measurement, and/or the like. The received measurements may be used to determine the breath cycle of the patient, for example, using any of the techniques described above.

At block 1206, the phase of the control signal may be matched with that of the breath cycle. This may comprise an iterative process, such as described above with reference to FIG. 8 and/or FIG. 9.

Figure 13:
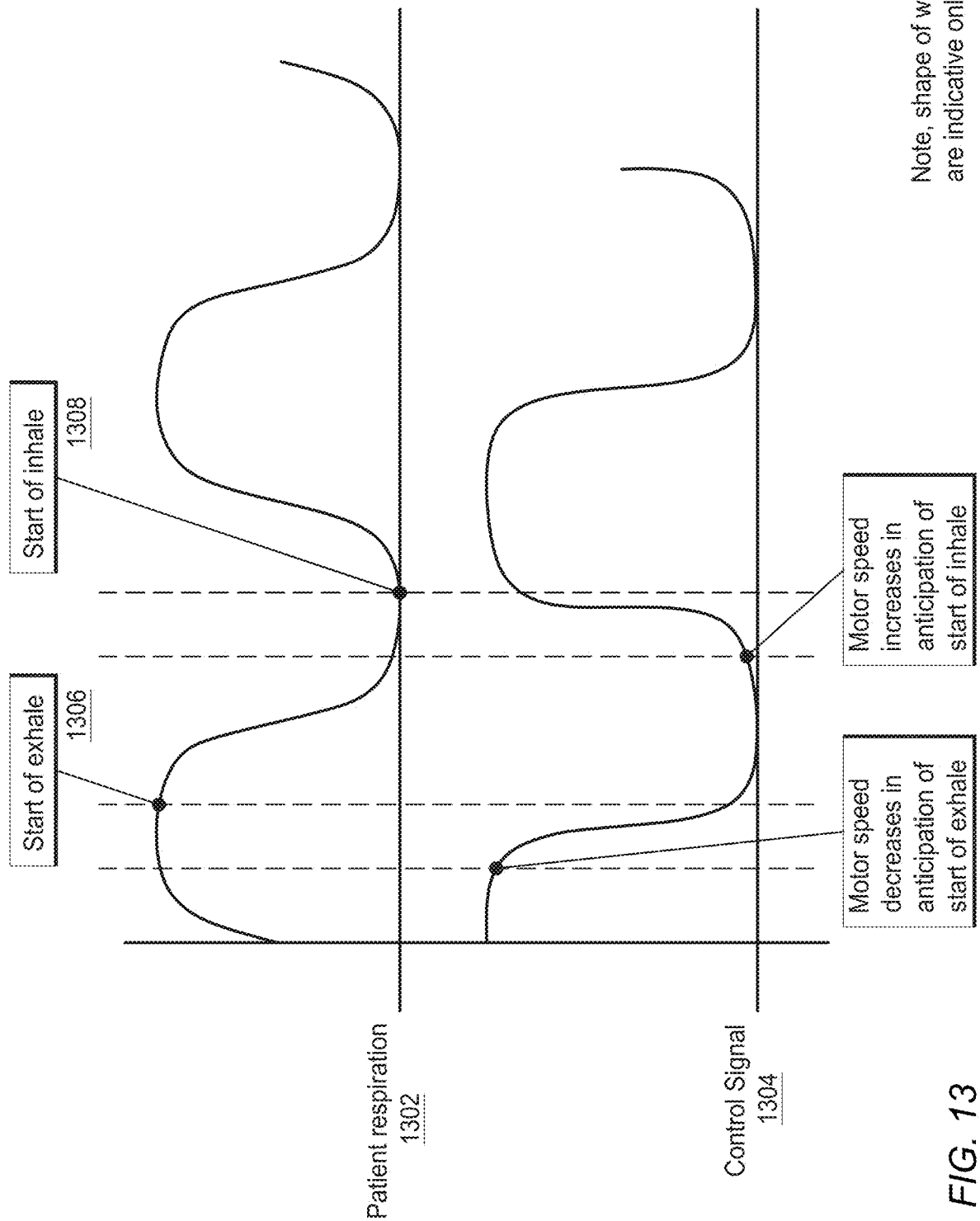
FIG. 13 illustrates an example chart of a patient breath cycle and a phase-shifted control loop.

At block 1208, the patient breath cycle is analysed to identify when the patient is inhaling or exhaling. For example, FIG. 13 illustrates an example chart of a patient breath cycle 1302 and a phase-shifted control signal 1304. As illustrated in FIG. 13, a patient may be inferred to begin exhaling near a peak of the patient's breath cycle waveform at (for example, shortly after the peak) at 1306, and to start inhaling near a valley of the breath cycle waveform (for example, shortly after the valley) at 1308.

Returning to FIG. 12 at block 1210, the phase of the control signal is shifted based upon the patient breath cycle. For example, the phase of the control signal may be shifted such that the control signal leads that of the breath cycle by a set amount of phase or time. For example, as illustrated in FIG. 13, the control waveform may be shifted such that the motor begins to decrease in speed before the patient begins exhaling, and to start increasing in speed before the patient begins inhaling.

The control waveform may be selected from a range of predefined shapes and modified based upon one or more breath parameters (for example, amplitude of the breath cycle waveform). The control waveform may be dynamically created based upon the sensed breath waveform.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The term "about" is employed herein to mean within standard measurement accuracy.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Certain acts, events, or functions of any of the algorithms, methods, or processes described herein can be performed in a different sequence, can be added, merged, or left out altogether (e.g., not all described acts or events are necessary for the practice of the algorithms). Moreover, acts or events can be performed concurrently, e.g., through multi-threaded processing, interrupt processing, or multiple processors or processor cores or on other parallel architectures, rather than sequentially.

It should be noted that various changes and modifications based on the present disclosure herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A respiratory therapy apparatus, comprising:
 a blower for generating an air flow for a patient, the blower being associated with a blower motor, wherein the blower motor is configured to be driven by a control signal;
 one or more sensors configured to measure at least a flow rate of the air flow; and
 a control system configured to:
  detect a breath cycle of the patient by:
   receiving a first input comprising one or more flow rate measurements from the one or more sensors,
   receiving a second input comprising one or more pressure measurements from at least one pressure sensor or one or more motor speed measurements associated with the blower motor, and
   generating a breath cycle waveform using at least the received flow rate measurements, wherein the breath cycle waveform comprises a plurality of alternating periods of the patient's inspiration and expiration, and
  synchronize the control signal with the breath cycle waveform by:
   identifying a phase of the breath cycle waveform, and
   iteratively updating a phase of the control signal to achieve a determined phase difference between the control signal and the breath cycle waveform, such that the control signal is configured to adjust a speed of the blower motor based upon the patient's inspiration and expiration;

wherein a magnitude of the control signal is determined based at least in part upon an amplitude of the breath cycle waveform.

2. The respiratory therapy apparatus of claim 1, wherein the control system is further configured to phase-shift the control signal based upon a system delay between the control signal being received by the blower motor and the resulting air flow being sensed.

3. The respiratory therapy apparatus of claim 1, wherein the control system is further configured to phase-shift the control signal, such that the control signal pre-empts the breath cycle waveform by a set amount of time.

4. The respiratory therapy apparatus of claim 1, wherein the one or more sensors comprises an ultrasonic sensor assembly.

5. The respiratory therapy apparatus of claim 1, wherein the one or more sensors further comprises a heated temperature sensing element.

6. The respiratory therapy apparatus of claim 1, wherein the control signal is phase-locked to the breath cycle waveform.

7. The respiratory therapy apparatus of claim 1, wherein the breath cycle waveform is used to calculate a patient breath rate.

8. The respiratory therapy apparatus of claim 1, wherein the magnitude of the control signal is further determined based at least in part upon a positive feedback parameter and a negative feedback parameter.

9. The respiratory therapy apparatus of claim 1, wherein the second input is the one or more motor speed measurements associated with the blower motor.

10. The respiratory therapy apparatus of claim 9, wherein the breath cycle waveform is generated using the received flow rate measurement and the one or more motor speed measurements.

11. The respiratory therapy apparatus of claim 9, wherein the breath cycle waveform is generated based at least in part upon a calculated patient flow, wherein the patient flow is based upon a system leak calculated using the received flow rate measurement and the one or more motor speed measurements.

12. The respiratory therapy apparatus of claim 9, wherein the one or more motor speed measurements are determined based at least in part upon one or more blower motor parameters.

13. The respiratory therapy apparatus of claim 1, wherein the blower motor comprises a brushless DC motor.

14. The respiratory therapy apparatus of claim 9, wherein the control system is configured to detect the breath cycle by receiving a third input comprising the one or more pressure measurements from the at least one pressure sensor.

15. The respiratory therapy apparatus of claim 1, wherein the second input is the one or more pressure measurements from the at least one pressure sensor.

16. The respiratory therapy apparatus of claim 1, wherein the respiratory therapy apparatus is a respiratory high flow therapy apparatus.

17. The respiratory therapy apparatus of claim 1, wherein the respiratory therapy apparatus is configured for use in a non-sealed respiratory system.

18. The respiratory therapy apparatus of claim 1, wherein the respiratory therapy apparatus is configured for use in a sealed respiratory system.

19. The respiratory therapy apparatus of claim 18, wherein the respiratory therapy apparatus is configured to adjust the speed of the blower motor to achieve a predetermined pressure of the sealed respiratory system based on the one or more pressure measurements from the at least one pressure sensor.

20. The respiratory therapy apparatus of claim 19, wherein the respiratory therapy apparatus is configured to be coupled with a non-invasive ventilation mask.

21. The respiratory therapy apparatus of claim 20, wherein the at least one pressure sensor is located in the non-invasive ventilation mask, or a manifold connecting the non-invasive ventilation mask to a patient breathing conduit, or within the patient breathing conduit, or within a housing of the respiratory therapy apparatus.

* * * * *